United States Patent
Merian et al.

(10) Patent No.: US 9,707,305 B2
(45) Date of Patent: Jul. 18, 2017

(54) FORMULAS FOR DIAGNOSING AND TREATING HORMONE-DEPENDENT CANCERS AND CANCERS OF THE ORGANS RESPONSIBLE FOR STEROID HORMONE SYNTHESIS

(71) Applicant: Commissariat à l'énergie atomique et aux énergies alternatives, Paris (FR)

(72) Inventors: Juliette Merian, Brive (FR); Raphaël Boisgard, Nozay (FR); Bertrand Tavitian, Paris (FR); Isabelle Texier-Nogues, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 645 days.

(21) Appl. No.: 14/349,822

(22) PCT Filed: Sep. 26, 2012

(86) PCT No.: PCT/EP2012/068944
§ 371 (c)(1),
(2) Date: Sep. 5, 2014

(87) PCT Pub. No.: WO2013/050280
PCT Pub. Date: Apr. 11, 2013

(65) Prior Publication Data
US 2015/0030543 A1     Jan. 29, 2015

(30) Foreign Application Priority Data
Oct. 5, 2011 (FR) .................................. 11 58991

(51) Int. Cl.
| | | |
|---|---|---|
| A61K 49/00 | (2006.01) |
| A61K 47/10 | (2017.01) |
| A61K 47/44 | (2017.01) |
| A61K 47/24 | (2006.01) |
| A61K 9/107 | (2006.01) |
| A61K 31/575 | (2006.01) |
| A61K 47/28 | (2006.01) |
| G01N 33/74 | (2006.01) |
| G01N 33/50 | (2006.01) |
| A61K 49/18 | (2006.01) |
| A61K 51/12 | (2006.01) |
| G01N 33/574 | (2006.01) |
| A61K 31/138 | (2006.01) |
| A61K 31/565 | (2006.01) |
| A61K 31/57 | (2006.01) |

(52) U.S. Cl.
CPC ........ *A61K 49/0078* (2013.01); *A61K 9/1075* (2013.01); *A61K 31/138* (2013.01); *A61K 31/565* (2013.01); *A61K 31/57* (2013.01); *A61K 31/575* (2013.01); *A61K 47/10* (2013.01); *A61K 47/24* (2013.01); *A61K 47/28* (2013.01); *A61K 47/44* (2013.01); *A61K 49/0032* (2013.01); *A61K 49/0034* (2013.01); *A61K 49/1806* (2013.01); *A61K 51/122* (2013.01); *G01N 33/5011* (2013.01); *G01N 33/57415* (2013.01); *G01N 33/57434* (2013.01); *G01N 33/57438* (2013.01); *G01N 33/57449* (2013.01); *G01N 33/743* (2013.01); *G01N 2333/723* (2013.01)

(58) Field of Classification Search
None
See application file for complete search history.

(56) References Cited

U.S. PATENT DOCUMENTS

| | | |
|---|---|---|
| 2010/0144899 A1 | 6/2010 | Goutayer et al. |
| 2011/0201695 A1 | 8/2011 | Mourier-Robert et al. |
| 2013/0251629 A1 | 9/2013 | Delmas et al. |

OTHER PUBLICATIONS

International Search Report for PCT/EP2012/068944 dated Nov. 20, 2012.
Almeida Cristina P et al: "Modification of composition of a nanoemulsion with different cholesteryl ester molecular species: effects on stability, peroxidation, and cell uptake.", International Journal of Nanomedicine 2010 LNKD—PUBMED:20957219, vol. 5, 2010, pp. 679-686.

*Primary Examiner* — Robert A Wax
*Assistant Examiner* — Randeep Singh
(74) *Attorney, Agent, or Firm* — B. Aaron Schulman, Esq.; Stites & Harbison, PLLC

(57) ABSTRACT

The present invention relates to a formulation of a therapeutic or diagnostic agent in the form of a nano-emulsion, to its preparation method and to the use of this formulation for treating or diagnosing hormone-dependent cancers or cancers of organs synthesizing steroidal hormones.

18 Claims, No Drawings

FORMULAS FOR DIAGNOSING AND TREATING HORMONE-DEPENDENT CANCERS AND CANCERS OF THE ORGANS RESPONSIBLE FOR STEROID HORMONE SYNTHESIS

The present invention relates to a formulation of the nano-emulsion type, to a method for its preparation as well as to its use for treating or diagnosing hormone-dependent cancers or cancers of organs synthesizing steroidal hormones.

STATE OF THE ART

Nanomedicine is a new field created by the merging of nanotechnology and of medicine, and is now one of the most promising routes for developing efficient targeted therapies or new diagnostic methods.

For this purpose, international applications WO 2010/018223 and WO 2008/102065 describe formulations in the form of nano-emulsions, comprising a continuous aqueous phase and at least one dispersed oily phase, wherein:
the oily phase comprises:
  at least one therapeutic agent (WO 2010/018223) or diagnostic agent (WO 2008/102065),
  at least one amphiphilic liquid, and
  at least one solubilizing lipid, and
the aqueous phase includes at least one co-surfactant comprising at least one chain consisting of alkylene oxide units.
These formulations are useful for delivering lipophilic or amphiphilic therapeutic agents or for optical imaging.

Moreover, cancer is the second cause of mortality worldwide. In France, it is estimated that one person out of three dies from cancer during his/her life. Among the most widespread, hormone-dependent cancers, for which cell proliferation depends on the presence of hormones: mainly estrogen for breast cancer and in majority androgen for prostate cancer. On the other hand, the organs for synthesizing steroidal hormones, such as ovaries or adrenal glands, may also be affected by cancers, often detected very late and difficult to treat.

Almeida et al. (Int. J. Nanomedicine, 5, 2010, 679-686) describes nano-emulsions comprising cholesteryl oleate, stearate or linoleate, egg phosphotidylcholine and cholesterol and triolein. This article teaches that nano-emulsions rich in cholesterol ester may be used as a delivery system for notably targeting tumors. This having been stated, this article by no means suggests that the described nano-emulsions may preferentially target hormone-dependent cancers as compared to non-hormone-dependent cancers. Further, the dispersed phases of the nano-emulsions comprise from 25 to 31% by weight of cholesteryl esters. Now, the inventors of the present application have shown that their nano-emulsions (notably described in international applications WO 2010/018223 and WO 2008/102065) could not be prepared with such proportions of cholesteryl esters. The development of new methods for diagnosis and treatment of hormone-dependent cancers and cancers of the organs synthesizing steroidal hormones is necessary.

TECHNICAL PROBLEM

For this purpose, the present invention provides a formulation which preferentially targets hormone-dependent cancers and cancers of organs synthesizing steroidal hormones. Thus, it is useful for the diagnosis or for the treatment of hormone-dependent cancers or cancers of organs synthesizing steroidal hormones.

DESCRIPTION OF THE INVENTION

[Definitions]

Within the scope of this discussion, by the term of <<nano-emulsion>> is meant a composition having at least two phases, generally an oily phase and an aqueous phase, wherein the average size of the dispersed phase is less than 1 micron, preferably from 10 to 500 nm and in particular from 20 to 100 nm, and most preferentially 20 and 70 nm (see the article C. Solans, P. Izquierdo, J. Nolla, N. Azemar and M. J. Garcia-Celma, Curr Opin Colloid In, 2005, 10, 102-110).

The term of <<droplet>> both encompasses, strictly speaking, liquid oil droplets and solid particles from emulsions of the oil-in-water type wherein the oily phase is solid. In the latter case, this is often also designated as a solid emulsion.

Within the sense of the present application, the expression of <<dispersed oily phase>> also called <<dispersed phase>> or <<oily phase>>, means the droplets comprising the optional oil/solubilizing lipid/amphiphilic lipid/co-surfactant (optionally grafted with a molecule of interest or with a diagnostic or therapeutic agent)/the compound of formula (I)/the optional therapeutic agent/the optional diagnostic agent. In particular for the calculations of the mass proportion of the compound of formula (I) relatively to the weight of the dispersed phase, it is considered that the co-surfactant belongs to the dispersed phase. The dispersed phase is generally free of aqueous phase.

The term of <<lipid>> designates within the scope of this discussion, the whole of the fats or substances containing fatty acids present in fats of animal origin and in vegetable oils. These are hydrophobic or amphiphilic molecules which mainly consist of carbon, hydrogen and oxygen and have a density below that of water. Lipids may be in the solid state at room temperature (25° C.), like in waxes, or liquid, like in oils.

The term of <<phospholipid>> aims at lipids having a phosphate group, notably phosphoglycerides. Most often, phospholipids include a hydrophilic end formed by the optionally substituted phosphate group and two hydrophobic ends formed by fatty acid chains. Among phospholipids, mention will in particular be made of phosphatidylcholine, phosphatidyl ethanolamine, phosphatidyl inositol, phosphatidyl serine and sphingomyelin.

The term of <<lecithin>> designates phosphatidylcholine, i.e. a lipid formed from a choline, a phosphate, a glycerol and two fatty acids. It more widely covers phospholipids extracted from living organisms, of vegetable or animal origin insofar that they in majority consist of phosphatidylcholine. These lecithins generally form mixtures of lecithins bearing different fatty acids.

The term of <<fatty acid>> is meant to designate aliphatic carboxylic acids having a carbonaceous chain of at least 4 carbon atoms. Natural fatty acids have a carbonaceous chain from 4 to 28 carbon atoms (generally an even number). One refers to a long chain fatty acid for a length of 14 to 22 carbons and to a very long chain if there are more than 22 carbons.

By the term of <<surfactant>> are meant compounds with an amphiphilic structure which give them particular affinity for interfaces of the oil/water and water/oil type, which gives them the possibility of lowering the free energy of the interfaces and of stabilizing dispersed systems.

By the term of <<co-surfactant>> is meant a surfactant acting in addition to a surfactant for further lowering the energy of the interface.

By the term of <<alkyl>> is meant a linear or branched saturated aliphatic hydrocarbon group. The alkyl group is preferably linear. By the term of <<alkenyl>> is meant a linear or branched, preferably linear aliphatic hydrocarbon group comprising at least one unsaturation in the form of a double bond.

In the sense of the present application, by the term of <<steroidic>> is meant a radical derived from a steroid by the loss of a hydrogen on one of the atoms of one of the rings of the steroid. By the term of <<sterolic>> is meant a radical derived from a sterol by the loss of a hydrogen on one of the atoms of one of the rings of the steroid. In the sense of the present application, steroids and sterols have the common IUPAC definition (International Union of Pure and Applied Chemistry) (Pure&Appl. Chem., Vol. 61, No. 10, pp. 1783-1822,1989). A steroid is a compound comprising a cyclopenta[a]phenanthrenic (sterane) ring which is partly or completely hydrogenated or a skeleton derived from the latter by splitting one or more bonds or by contractions or expansions of rings. Preferred steroids are those comprising a partly or completely hydrogenated cyclopenta[a]phenanthrenic (sterane) ring. A sterol is a steroid comprising a hydroxyl group in position C3.

[Emulsion]

According to a first aspect, the invention relates to a formulation of a therapeutic or diagnostic agent in the form of a nano-emulsion, comprising a continuous aqueous phase and at least one dispersed oily phase, wherein:
the oily phase comprises:
    at least one amphiphilic lipid,
    at least one solubilizing lipid,
    at least one compound of the following formula (I):

(R-L)$_n$-A    (I), wherein:
    n represents an integer from 1 to 5, notably from 1 to 2, preferably 1,
    L represents a simple bond or a divalent group selected from —O—, —COO—, —OOC—, —CO—NR'—, —NR'—CO—, —S—, —NR'—CO—NR"—, —O—CO—O—, wherein R' and R" independently represent H or a linear or branched alkyl with 1 to 20 carbon atoms and
    R represents a linear or branched alkyl comprising at least 11 carbon atoms or a linear or branched alkenyl comprising at least 11 carbon atoms, and
    A represents a steroidic or sterolic group,
    the aqueous phase includes at least one co-surfactant comprising at least one chain consisting of alkylene oxide units.

The emulsion is therefore an emulsion of the oil-in-water type. It may be simple or multiple, notably by including a second aqueous phase in the dispersed phase. Preferably, it is simple.

Compound of Formula (I)

The emulsion comprises at least one compound comprising a steroidic or sterolic group A bound through at least one group L to a hydrocarbon chain comprising at least 11 carbon atoms (group R).

In the formulation according to the invention, the compound of formula (I) is notably useful as a diagnostic agent or therapeutic agent for treating hormone-dependent cancers or cancers of organs synthesizing steroidal hormones.

In an embodiment, the group A is a group having one of the following formulae:

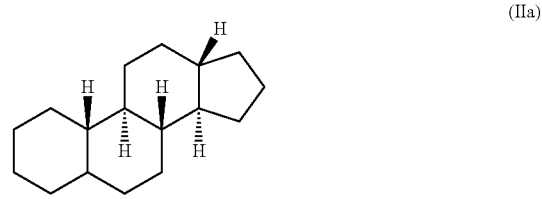
(IIa)

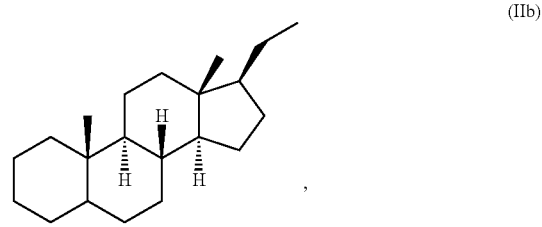
(IIb)

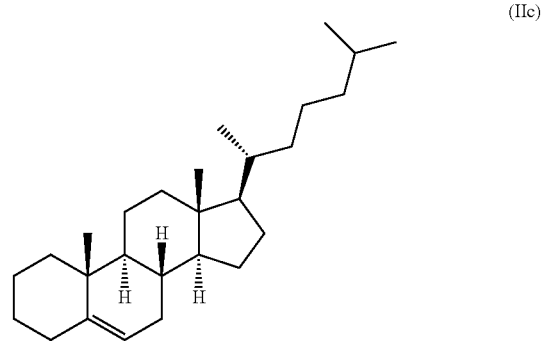
(IIc)

wherein one or more of the carbon atoms are substituted with a group -L-R.

In a preferred embodiment, the group A is substituted in position C3 with a group -L-R. The compound of the following formula (III) is more preferred:

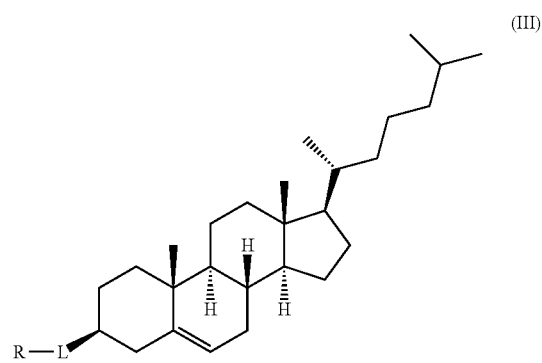
(III)

When L is a group —O— or —COO—, the compound of formula (III) is respectively a cholesteryl ether or ester.

The compound of formula (I) comprises n groups -L-R.

Preferably, n represents 1, i.e. the compound of formula (I) comprises a steroidic or sterolic group substituted once with an -L- R group.

R represents an alkyl or an alkenyl comprising at least 11 carbon atoms, notably from 11 to 25 carbon atoms, preferably from 11 to 19 carbon atoms.

L represents a simple bond or a divalent group selected from —O—, —COO—, —OOC—, —CO—NR'—, —NR'—CO—, —S—, —NR'—CO—NR"—, —O—CO—O—. Preferably, L represents a divalent group. R' and R" independently represent H or a linear or branched alkyl with 1 to 20 carbon atoms, notably H or a methyl, preferably H.

In a preferred embodiment, L represents —O— or —COO—. When L represents an ester function —COO—, it is inferred that the group R is bound to the carbon atom of —COO— and the group A is bound to the oxygen atom of —COO—.

L preferably represents —COO—. The compound then has the formula (IV):

(R—COO)$_n$-A  (IV)

wherein R, n and A are as defined above. Preferably, n represents 1 and the compound has the following formula (V):

R—COO-A  (V)

Indeed, the ester function may advantageously be metabolized, which allows the organism to which the formulation according to the invention is administered, to eliminate the compound of formula (I) in which L represents —COO—. As a comparison, the compounds of formula (I) wherein L represents —O— tend to accumulate in the organism. Preferably, the compound has the following formula (VI):

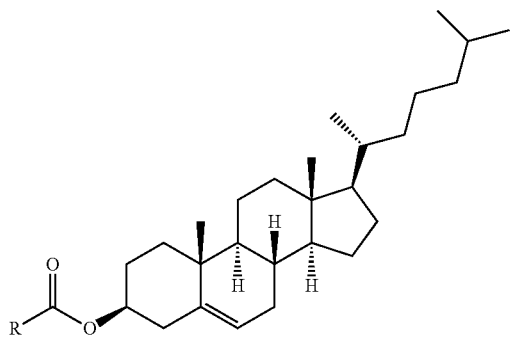

(VI)

wherein R is as defined above.

Preferably, the compound of formula (IV), (V) or (VI) (formulae wherein L represents —COO—) is a saturated or unsaturated fatty acid ester, notably selected from the following esters:

|  | R | Compound of formula (IV) or (V) | Compound of formula (VI) |  |
|---|---|---|---|---|
| alkyl | $CH_3(CH_2)_{10}$— | Steroidic or sterolic laurate | Cholesteryl laurate | Saturated fatty ester |
|  | $CH_3(CH_2)_{12}$— | Steroidal or sterolic myristate | Cholesteryl myristate |  |
|  | $CH_3(CH_2)_{14}$— | Steroidic or sterolic palmitate | Cholesteryl palmitate |  |
|  | $CH_3(CH_2)_{16}$— | Steroidic or sterolic stearate | Cholesteryl stearate |  |
|  | $CH_3(CH_2)_{18}$— | Steroidic or sterolic arachidate | Cholesteryl achidate |  |
|  | $CH_3(CH_2)_{20}$— | Steroidic or sterolic behenate | Cholesteryl behenate |  |
|  | $CH_3(CH_2)_{22}$— | Steroidic or sterolic lignocerate | Cholesteryl lignocerate |  |
|  | $CH_3(CH_2)_{24}$— | Steroidic or sterolic cerotate | Cholesteryl cerotate |  |
| alkenyl | $CH_3(CH_2)_3CH=CH(CH_2)_7$— | Steroidic or sterolic myristoleate | Cholesteryl myristoleate | Unsaturated fatty acid |
|  | $CH_3(CH_2)_5CH=CH(CH_2)_7$— | Steroidic or sterolic palmitoleate | Cholesteryl palmitoleate |  |
|  | $CH_3(CH_2)_7CH=CH(CH_2)_7$— | Steroidic or sterolic oleate | Cholesteryl oleate |  |
|  | $CH_3(CH_2)_7CH=CH(CH_2)_7$— | Steroidal or sterolic elaidate | Cholesteryl elaidate |  |
| alkenyl | $CH_3(CH_2)_5CH=CH(CH_2)_9$— | Steroidic or sterolic vaccenate | Cholesteryl vaccenate | Unsaturated fatty acid |
|  | $CH_3(CH_2)_4CH=CHCH_2CH=CH(CH_2)_7$— | Steroidic or sterolic linoleate | Cholesteryl linoleate |  |
|  | $CH_3(CH_2)_4CH=CHCH_2CH=CH(CH_2)_7$— | Steroidic or sterolic linoelaidate | Cholesteryl linoelaidate |  |

-continued

| R | Compound of formula (IV) or (V) | Compound of formula (VI) |
|---|---|---|
| $CH_3CH_2CH=CHCH_2CH=CHCH_2CH=CH(CH_2)_7—$ | Steroidic or sterolic α-linolenate | Cholesteryl α-linolenate |
| $CH_3(CH_2)_4CH=CHCH_2CH=CHCH_2CH=CHCH_2CH=CH(CH_2)_3—$ | Steroidic or sterolic arachidonate | Cholesteryl arachidonate |
| $CH_3CH_2CH=CHCH_2CH=CHCH_2CH=CHCH_2CH=CHCH_2CH=CH(CH_2)_3—$ | Steroidic or sterolic eicosapentaenate | Cholesteryl eicosapentaenate |
| $CH_3(CH_2)_7CH=CH(CH_2)_{11}—$ | Steroidic or sterolic erucate | Cholesteryl erucate |
| $CH_3CH_2CH=CHCH_2CH=CHCH_2CH=CHCH_2CH=CHCH_2CH=CHCH_2CH=CH(CH_2)_2—$ | Steroidic or sterolic docosahexaenate | Cholesteryl docosahexaenate |

Among the compounds of formula (I) wherein L represents —COO—, cholesteryl stearate and cholesteryl oleate are more preferred.

Among the compounds of formula (I) wherein L represents —O—, cholesteryl hexadecylether is preferred.

The compound of formula (I) is in majority (more than 50%) localized in the dispersed oily phase of the nano-emulsion, and in minority (less than 50%) in the continuous aqueous phase. In the present application, the mass percentages of dispersed phase, as described, are calculated by considering that the compound of formula (I) belongs to the dispersed phase.

The compounds of formulae (I) are available commercially and may be synthesized with methods known to one skilled in the art. For example, when L represents —O— or —COO— and A cholesteryl, the compounds may be obtained by etherification or esterification of cholesterol.

Generally, in the formulation according to the invention, the proportion of compound of formula (I) is less than 3% by weight, and is notably between 0.05 and 3% by weight, preferably between 0.3 and 2.5% by weight, based on the weight of the dispersed phase of the nano-emulsion (the weight of the co-surfactant being included in the weight of the dispersed phase). More specifically, the ratio of the mass of compound of formula (I) over the whole of the masses of the (optional oil/solubilizing lipid/amphiphilic lipid/co-surfactant (optionally grafted with a molecule of interest or with a diagnostic or therapeutic agent)/the compound of formula (I)/the optional therapeutic agent/the optional diagnostic agent) is less than 3%. Indeed, for these proportions, the size of the droplets is generally more homogeneous, which allows a more homogeneous release of the therapeutic or diagnostic agent. Further, for larger proportions, it is not generally possible to prepare the nano-emulsion. Without intending to be bound to a particular theory, it would seem that beyond 3% by weight, the compound of formula (I) does not in majority solubilize in the dispersed oily phase of the nano-emulsion.

In a preferred embodiment, the oily phase of the formulation according to the invention further comprises at least one therapeutic agent for treating hormone-dependent cancers or cancers of organs synthesizing steroidal hormones, or a diagnostic agent (in addition to the compound of formula (I)).

Advantageously, as the therapeutic or diagnostic agent is encapsulated in droplets of the nano-emulsion, the formulation according to the invention protects the body into which the formulation is administered from said agent (the latter will essentially be located at the hormone-dependent cancer or at the cancer of the organs synthesizing steroidal hormones, and a little elsewhere in the body) and also protects the agent from the body (notably by avoiding its premature metabolism).

The diagnostic agent may notably be used in imaging of the type:

Positron Emission Tomography (PET) (the diagnostic agent may be a compound comprising a radionuclide, such as $^{18}F$, $^{11}C$, a chelate of metal cations $^{68}Ga$, $^{64}Cu$), Single Photon Emission Computed Tomography (SPECT) (the diagnostic agent may be a compound comprising a radionuclide for example $^{123}I$, or a chelate of $^{99m}Tc$ or $^{111}In$), Magnetic Resonance Imaging (MRI) (the diagnostic agent may be a chelate of gadolinium or a magnetic nanocrystal such as a nanocrystal of iron oxide, magnesium oxide or iron-platinum FePt), optical imaging or X-ray imaging (the diagnostic agent may be a lipophilic fluorophore or a contrast agent, for example an iodine-containing molecule such as iopamidol, amidotrizoate or gold nanoparticles).

Preferably, the diagnostic agent is a lipophilic fluorophore giving the possibility of achieving optical imaging.

The nature of the lipophilic fluorophore(s) which may be used is not critical from the moment that they are compatible with in vivo imaging (i.e. they are biocompatible and non-toxic). Preferably, the fluorophores used as a diagnostic agent absorb and emit in the visible spectrum and in the near infrared, in particular in the near infrared. Indeed, in order that the excitation light and the light emitted by the fluorophore may better cross the tissues, fluorophores which absorb and emit in the near infrared, i.e. as a wavelength comprised between 640 and 900 nm, should be used.

As a lipophilic fluorophore, mention may for example be made of the compounds described in chapter 13 ("Probes for Lipids and Membranes") of the InVitrogen catalog. More specifically, mention may notably be made, as a fluorophore, of indocyanine green (ICG), fatty acid analogues and phospholipids functionalized with a fluorescent group such as the fluorescent products sold under the commercial names of Bodipy (R) such as Bodipy (R) 665/676 (Ex/Em.); amphiphilic derivatives of dialkylcarbocyanines such as 1,r-dioctadécyl-3,3,3',3'-tetramethylindodicarbocyanine (DiD) perchlorate, for example sold under reference D-307; fluorescent probes derived from sphingolipids, steroids or lipopolysaccharides such as the products sold under the commercial names BODIPY® TR ceramides, BODIPY® FL C5-lactosylceramide, BODIPY® FL C5-ganglioside, BODIPY® FL cerebrosides; amphiphilic derivatives of cyanines (such as 1,1'-dioctadecyl-,3,3,3',3'-etramethylindodicarbocyanine (DiD) perchlorate), rhodamines, fluoresceins, or cumarins such as octadecyl rhodamine B, fluorescein octadecyl ester and 4-heptadecyl-7-hydroxycumarin; and diphenylhexatriene (DPH) and derivatives thereof; the whole of these products being sold by the Invitrogen corporation.

According to a preferred embodiment of the invention, the fluorophore is indocyanine green or 1,r-dioctadecyl-3,3, 3',3'-tetramethylindodicarbocyanine perchlorate.

The therapeutic agent for treating hormone-dependent cancers or cancers of organs synthesizing steroidal hormones is notably selected from:
- agonists of gonadoliberin (or GnRH, acronym of <<Gonadotropin Releasing Hormone>>, or further LHRH, acronym of <<Luteinizing Hormone Releasing Hormone>>), such as estrogen or progestins,
- antagonists of aromatase, such as Formestane, Exemstane, Aminoglutethimide, Anastrozole, Fadrozole, Letrozole, Megestrol acetate, Medroxyprogesterone acetate or Mifepristone, and
- anti-estrogens (for treating breast cancer) such as Tamoxifene or Fulvestrant or anti-androgens (for treating prostate cancer), such as abiraterone acetate or cyproterone acetate.

Of course, the therapeutic agent may be directly formulated in its active form or in the form of a prodrug.

Moreover, it is contemplated that several therapeutic and/or diagnostic agents may be formulated associated together in the nano-emulsion.

It is generally sought to formulate the nano-emulsion with a maximum concentration of therapeutic or diagnostic agent, notably when these are not very soluble agents, in order to limit the volume and/or the duration of administration to the patient. Now, it has been noticed that the presence of the solubilizing lipid in the oily phase gives the possibility of incorporating a large amount of the agents, even hydrophobic or amphiphilic agents.

The formulation according to the invention will most often contain an amount from 0.001 to 30% by weight, preferably 0.01 to 20% by weight, and still preferably 0.1 to 10% by weight of a therapeutic or diagnostic agent.

Advantageously, the agents are incorporated into the emulsion in the form of a solution, and the solvent is then separated, for example by evaporation. The solution contains the therapeutic or diagnostic agent in a variable amount which may range up to its solubility limit. The selection of the solvent depends on the solubility of each therapeutic or diagnostic agent. The solvents used may for example be methanol, ethanol, chloroform, dichloromethane, hexane, cyclohexane, DMSO, DMF or further toluene. Preferably these are volatile solvents, preferably non-toxic for humans.

According to the invention, the oily phase of the nano-emulsion includes at least one amphiphilic lipid and at least one solubilizing lipid.

In order to form a stable nano-emulsion, it is generally necessary to include in the composition at least one amphiphilic lipid as a surfactant. The amphiphilic nature of the surfactant ensures stabilization of the oil droplets within the aqueous continuous phase.

Amphiphilic lipids include a hydrophilic portion and a lipophilic portion. They are generally selected from compounds for which the lipophilic portions comprise a linear or branched, saturated or unsaturated chain, having from 8 to 30 carbon atoms. They may be selected from phospholipids, cholesterols, lysolipids, sphingomyelins, tocopherols, glucolipids, stearylamines, cardiolipins of natural or synthetic origin; the molecules consisting of a fatty acid coupled with a hydrophilic group through an ether or ester function such as sorbitan esters like for example sorbitan monooleate and monolaurate sold under the names of Span® by Sigma; polymerized lipids; lipids conjugate with short polyethylene oxide (PEG) chains such as the non-ionic surfactants sold under the commercial names of Tween® by ICI Americas, Inc. and Triton® by Union Carbide Corp.; sugar esters such as saccharose mono- and di-laurate, mono- and di-palmitate, mono- and di-stearate; said surfactants may be used alone or as mixtures.

Phospholipids are the preferred amphiphilic lipids.

Lecithin is the more preferred amphiphilic lipid.

According to a particular embodiment, all or part of the amphiphilic lipid may have a reactive function, such as a maleimide, thiol, amine, ester, oxyamine or aldehyde group. The presence of reactive functions allows marking of functional compounds at the interface. The reactive amphiphilic lipid is incorporated into the layer formed at the interface stabilizing the dispersed phase, where it may for example be coupled with a reactive compound present in the aqueous phase.

Generally, the oily phase will include from 0.01 to 99% by weight, preferably from 5 to 75% by weight, in particular from 10 to 50% and most particularly from 10 to 30% by weight of amphiphilic lipid.

The amount of amphiphilic lipid advantageously contributes to controlling the size of the dispersed phase of the obtained nano-emulsion.

The emulsion according to the invention moreover comprises a solubilizing lipid. This compound has the main mission of solubilizing the not very soluble amphiphilic lipid in the oily phase of the nano-emulsion.

The solubilizing lipid is a lipid having sufficient affinity with the amphiphilic lipid for allowing its solubilization. Preferably the solubilizing lipid is solid at room temperature.

In the case when the amphiphilic lipid is a phospholipid, these may notably be derivatives of glycerol, and in particular glycerides obtained by esterification of glycerol with fatty acids.

The solubilizing lipid used is advantageously selected according to the amphiphilic lipid used. It will generally have a close chemical structure, in order to ensure the sought solubilization. This may be an oil or a wax. Preferably, the solubilizing lipid is solid at room temperature (20° C.), but liquid at the temperature of the body (37° C.).

The preferred solubilizing lipids, in particular for phospholipids, are the glycerides of fatty acids, notably of saturated fatty acids, and in particular of saturated fatty acids including from 8 to 18 carbon atoms, still preferably from 12 to 18 carbon atoms. Advantageously, this is a mixture of different glycerides.

Preferably, these are glycerides of saturated fatty acids including at least 10% by weight of C12 fatty acids, at least 5% by weight of C14 fatty acids, at least 5% by weight of C16 fatty acids and at least 5% by weight of C18 fatty acids.

Preferably, these are glycerides of saturated fatty acids including 0% to 20% of C8 fatty acids, 0% to 20% by weight of C10 fatty acids, 10% to 70% by weight of C12 fatty acids, 5% to 30% by weight of C14 fatty acids, 5% to 30% by weight of C16 fatty acids and 5% to 30% by weight of C18 fatty acids.

The mixtures of semi-synthetic glycerides solid at room temperature sold under the trade name Suppocire®NC by Gattefossé and approved for injection in humans are particularly preferred. The Suppocire® of type N are obtained by direct esterification of fatty acids and of glycerol. These are hemi-synthetic glycerides of saturated C8-C18 fatty acids, the qualitative-quantitative composition of which is indicated in the table below.

The aforementioned solubilizing lipids give the possibility of obtaining a formulation in the form of an advantageously stable nano-emulsion. Without intending to be bound to a particular theory, it is assumed that the aforementioned solubilizing lipids give the possibility of obtaining droplets in the nano-emulsion having an amorphous core. The thereby obtained core has a high internal viscosity without however exhibiting crystallinity. Now crystallization is detrimental to the stability of the nano-emulsion since it generally leads to aggregation of the droplets and/or to expulsion of the encapsulated molecules on the outside of the droplets. These physical properties promote the physical stability of the nano-emulsion and the stability of the encapsulation over time of the therapeutic or diagnostic agent.

The amount of solubilizing lipid may widely vary according to the nature and to the amount of amphiphilic lipid present in the oily phase. Generally, the oily phase will include from 1 to 99% by weight, preferably from 5 to 80% by weight and most particularly from 40 to 75% by weight of solubilizing lipid.

| Fatty acid composition of Suppocire ® NC from Gattefossé | |
|---|---|
| Length of chains | [% by weight] |
| C8 | 0.1 to 0.9 |
| C10 | 0.1 to 0.9 |
| C12 | 25 to 50 |
| C14 | 10 to 24.9 |
| C16 | 10 to 24.9 |
| C18 | 10 to 24.9 |

The oily phase may moreover include one or several other oils.

The oils used preferably have a hydrophilic-lipophilic balance (HLB) of less than 8 and still more preferentially comprised between 3 and 6. Advantageously, the oils are used without any chemical or physical modification before the formation of the emulsion.

According to the contemplated applications, the oils may be selected from biocompatible oils, and in particular from oils of natural origin (plant or animal) or of synthetic origin. Among such oils, mention may notably be made of oils of natural plant origin among which notably appear soybean, flax, palm, groundnut, olive, grape pip and sunflower oils; the synthetic oils among which triglycerides, di-glycerides and mono-glycerides notably appear. These oils may be of first expressions, refined or inter-esterified.

The preferred oils are soybean oil and flax oil.

Generally, if present, the oil will be contained in the oily phase in a proportion ranging from 1 to 80% by weight, preferably between 5 and 50% by weight and most particularly 10 to 30% by weight.

The oily phase may further contain other additives such as coloring agents, stabilizers, preservatives or other active ingredients, in a suitable amount.

The oily phase for the dispersed phase of the emulsion may be prepared by simply mixing the constituents, if necessary by heating them until the whole of the constituents melt.

The aqueous phase of the nano-emulsion according to the invention preferably consists of water and/or of a buffer such as a phosphate buffer like for example Phosphate Buffer Saline (PBS) or a saline solution, notably a sodium chloride solution.

The proportion of the oily phase and of the aqueous phase is very variable. However, most often, the nano-emulsions will be prepared with 1 to 50%, preferably 5 to 40% and most particularly 10 to 30% by weight of oily phase and 50 to 99%, preferably 60 to 95% and most particularly 70 to 90% by weight of aqueous phase.

Further, the aqueous phase optionally includes other ingredients, including a co-surfactant. The co-surfactant allows stabilization of the nano-emulsion.

The co-surfactant may moreover have other effects in the contemplated application of the nano-emulsion.

The co-surfactants which may be used in the emulsion according to the present invention are preferably water-soluble surfactants. Thus, the co-surfactant is located both in the continuous aqueous phase and in the dispersed phase. Indeed, the hydrophobic portion of the co-surfactant is inserted into the droplets of the dispersed phase, while the polyalkoxylated chains are in the continuous aqueous phase. In the present application, the mass percentages of dispersed phase, as described, are calculated by considering that the co-surfactant belongs to the dispersed phase.

The water-soluble surfactants are preferably alkoxylated (they comprise at least one chain consisting of alkylene oxide units) and preferably include at least one chain consisting of ethylene oxide units or ethylene oxide and propylene oxide (PEO or PEG) units. Preferably, the number of units in the chain varies between 2 and 500.

As an example of co-surfactants, mention may in particular be made of polyethylene glycol/phosphatidyl-ethanolamine (PEG-PE) conjugate compounds, fatty acid and polyethylene glycol ethers as well as products sold under the trade names of Brij® (for example Brij® 35, 58, 78 or 98) by ICI Americas Inc., fatty acid and polyethylene glycol esters such as the products sold under the trade name Myrj® by ICI Americas Inc. (for example Myrj® 45, 52, 53 or 59) and the ethylene oxide and propylene oxide block copolymers as well as the products sold under the trade names Pluronic® by BASF AG (for example Pluronic® F68, F127, L64, L61, 10R4, 17R2, 17R4, 25R2 or 25R4) or the products sold under the trade name Synperonic® by Unichema Chemie BV (for example Synperonic® PE/F68, PE/L61 or PE/L64).

The aqueous phase includes from 0.01 to 50% by weight, preferably from 1 to 30% by weight and most particularly from 4 to 20% by weight of co-surfactants.

According to a preferred embodiment, the dispersed phase of the nano-emulsion is grafted at the surface with molecules of interest such as biological ligands. Such grafting allows specific recognition of certain cells or of certain organs. Preferably, the grafting at the surface is achieved by coupling of the molecules of interest or of their precursors with an amphiphilic compound, notably with the co-surfactant. The nano-emulsion then comprises a grafted co-surfactant. In this case, the amphiphilic compound plays the role of a spacer allowing the molecules of interest to be accommodated at the surface.

The molecules of interest may for example be:
biological targeting ligands such as antibodies, peptides, saccharides, aptamers, oligonucleotides or compounds like folic acid;
a stealth agent: an added entity for giving stealthiness towards the immune system, to increase its circulation time in the organism, and to slow down its elimination.

For example, when the biological ligand is a peptide comprising one or more cysteines, the grafting to the alkylene oxide chain of the surfactant may be ensured by thiol-maleimide coupling.

In an embodiment, the diagnostic or therapeutic agent is grafted onto the co-surfactant. The grafting is typically ensured by a covalent bond between the co-surfactant and the diagnostic or therapeutic agent. With this embodiment, it is possible to impose that the diagnostic or therapeutic agent be located at the surface of the droplets of the nano-emulsion, at the interface between the continuous phase and the dispersed phase, which is notably advantageous when the diagnostic agent has a short half-life duration, for example, for diagnostic agents comprising $^{18}F$ having a half-life of 118 minutes.

In an embodiment, the co-surfactant of the nano-emulsion is a mixture of co-surfactants comprising a co-surfactant grafted with a diagnostic or therapeutic agent, a co-surfactant grafted with a molecule of interest and optionally a non-grafted co-surfactant.

According to an embodiment, the continuous aqueous phase also includes a thickening agent such as a glycerol, a saccharide, an oligosaccharide or a polysaccharide, a gum or further a protein, preferably glycerol. Indeed, the use of a continuous phase with a higher viscosity facilitates emulsification and consequently allows reduction in the sonication time.

The aqueous phase advantageously includes from 0 to 50% by weight, preferably from 1 to 30% by weight and most particularly from 5 to 20% by weight of a thickening agent.

Of course, the aqueous phase may further contain other additives such as coloring agents, stabilizers and preservatives in a suitable amount.

The aqueous phase for the continuous phase of the emulsion may be prepared by simply mixing the different constituents with the selected aqueous medium.

The formulation according to the invention is advantageously stable: it may be stored for more than three months without any degradation being observed. Moreover, the zeta potential of the dispersed phase is less than 20 mV in absolute value, i.e. comprised between −20 and +20 mV. The high absolute value of the zeta potential of the droplets has the effect of accumulation in the body, notably in the liver, the spleen, the lungs in addition to the kidneys. Now, in particular for the imaging applications, inversely a stealth formulation is sought, which has a long plasma lifetime after intravenous injection.

[Preparation Method]

The nano-emulsion as described may easily be prepared by dispersing suitable amounts of oily phase and of aqueous phase under the effect of shearing.

Within the scope of the method according to the invention, the different oily constituents, the compound of formula (I) and optionally the therapeutic or diagnostic agents are first mixed in order to prepare an oily premix for the dispersed phase of the emulsion. The preparation method typically comprises the following steps:

(i) prepare the oily phase comprising at least one solubilizing lipid, at least one amphiphilic lipid, optionally at least one therapeutic or diagnostic agent and at least one compound of formula (I);
(ii) prepare an aqueous phase comprising a polyalkoxylated co-surfactant;
(iii) disperse the oily phase in the aqueous phase under the action of sufficient shearing for forming a nano-emulsion; and
(iv) recover the thereby formed nano-emulsion.

The mixture may optionally be facilitated by putting one of the constituents or of the complete mixture in solution in a suitable organic solvent. The organic solvent is then evaporated, in order to obtain a homogeneous oily premix for the dispersed phase.

Moreover, the premix is preferably made (step (i)) at a temperature at which the whole of the ingredients are liquid.

Advantageously, the oily phase is dispersed in the aqueous phase in the liquid state. If one of the phases solidifies at room temperature, the mixing is preferably carried out with one or preferably both phases being heated to a temperature greater than or equal to the melting temperature.

The emulsification under the effect of shearing is preferably achieved by means of a sonicator or a microfluidizer. Preferably, the aqueous phase and the oily phase are then introduced in the desired proportions into a suitable cylindrical container and then the sonicator is immersed into the medium and started for sufficient time in order to obtain a nano-emulsion, most often a few minutes.

A homogeneous nano-emulsion is then obtained in which the average diameter of the oil droplets is greater than 10 nm and less than 200 nm, preferably between 20 and 50 nm.

Preferably, the zeta potential is less than 20 mV in absolute value, i.e. comprised between −20 mV and +20 mV.

Before its conditioning, the emulsion may be diluted and/or sterilized, for example by filtration or dialysis. This step allows removal of the possible aggregates which may be formed during the preparation of the emulsion.

The thereby obtained emulsion is ready-to-use, if necessary after dilution.

In embodiments in which the nano-emulsion comprises a grafted co-surfactant, the preparation method typically comprises the following steps:
(i) preparing the oily phase comprising at least one solubilizing lipid, at least one amphiphilic lipid, optionally at least one therapeutic or diagnostic agent and at least one compound of formula (I);
(ii) preparing an aqueous phase comprising a polyalkoxylated co-surfactant and a function capable of reacting with the compound to be grafted (molecules of interest or diagnostic or therapeutic agent);
(iii) dispersing the oily phase in the aqueous phase under the action of sufficient shearing for forming a nano-emulsion;
(iv) adding to the nano-emulsion the compound to be grafted under conditions allowing grafting between the function which may react with the compound to be grafted of the co-surfactant and the compound to be grafted,
(v) recovering the thereby formed nano-emulsion.

The grafting is therefore typically carried out after forming the nano-emulsion, which may be recommended when the chemical reactions used are compatible with the colloidal stability of the emulsions, notably in terms of pH. Preferably, the pH during the grafting reaction is comprised between 5 and 11.

In another embodiment, the preparation method comprises the following steps:

(i) providing a polyalkoxylated co-surfactant grafted with the compound to be grafted (molecules of interest or diagnostic or therapeutic agent),
(ii) preparing the oily phase comprising at least one solubilizing lipid, at least one amphiphilic lipid, optionally at least one therapeutic or diagnostic agent and at least one compound of formula (I);
(iii) preparing an aqueous phase comprising the polyalkoxylated co-surfactant grafted with the compound to be grafted;
(iv) dispersing the oily phase in the aqueous phase under the action of sufficient shearing for forming a nano-emulsion;
(v) recovering the thereby formed nano-emulsion.

The polyalkoxylated co-surfactant grafted with the compound to be grafted being generally obtained by putting the compound to be grafted in contact with a co-surfactant comprising a function which may react with the compound to be grafted, under conditions allowing grafting between the functions capable of reacting with the compound to be grafted of the co-surfactant and the compound to be grafted.

[Use]

When it is administered, the formulation according to the invention preferentially targets hormone-dependent cancers, notably breast or prostate cancers, and cancers of organs synthesizing steroidal hormones, notably ovaries and adrenal glands. The specificity of a hormone-dependent cancer is that it synthesizes its own steroidal hormones in the tumor itself.

Without intending to be bound to particular theories, the preferential targeting of the tumors (regardless of their type) may be explained by the permeability and retention effect (Enhanced Permeability and Retention (EPR)) due to the size of the droplets of the dispersed phase. The EPR effect is the property which molecules of certain sizes have (here the droplets of the emulsion according to the invention) of preferentially accumulating in the tumoral tissue relatively to the normal tissue. Indeed, the tumoral tissue has an irregularity at the vessels which feed it allowing the molecules of certain sizes (typically liposomes, nanoparticles or drugs, here the droplets of the nano-emulsions) to preferentially accumulate in the tumoral tissue relatively to the normal tissue. Indeed, tumoral cells have fast growth and have to form as fast as possible new vessels which will allow them to be provided with oxygen and with nutrients required for their growth. Due to fast synthesis, these new vessels will have an abnormal shape and an irregular architecture. As the cells are no longer aligned, they exhibit fenestrations through which the nanoparticles will be able to slip in and enter the inside of the tumor. Further, tumoral tissue has low lymphatic drainage, which will promote the retention of the nanoparticles within the tissue [Maeda H, Wu J, Sawa T, Matsumura Y, Hon K, J Control Release, 65, 271-284, 2000.].

Further, it seems that the formulation according to the invention has strong affinity for the synthesis areas of steroidal hormones, and therefore for the hormone-dependent cancers or the cancers of organs synthesizing steroidal hormones, for which survival, growth and cell proliferation are sensitive to the presence of steroidal hormones: preferentially estrogens for breast cancer and preferentially androgens for prostate cancer. First of all, the cells generally comprise many lipids. Cancer cells would therefore use the amphiphilic and solubilizing lipids of the formulation according to the invention. Further, the compound of formula (I) of the formulation according to the invention has a structure close to the precursors used by the body for synthesizing steroidal hormones. Indeed, the compound of formula (I) comprises a group A, for which the backbone is steroidic. Thus, the formulation according to the invention provides the cancer cells of these cancers, with precursors required for their proliferation. The droplets of the formulation according to the invention would be preferentially attracted by the synthesis area of steroidal hormones of the tumor.

This theory might suggest that a formulation comprising any compound including a steroidal backbone, such as cholesterol, instead of the compound of formula (I) would allow specific targeting of the steroidal organs. This is not the case. The particular structure of the compounds of formula (I), which comprise a steroidic or sterolic group and a carbonaceous chain is significant. Indeed, a formulation in which the compound of formula (I) is replaced with cholesterol does not have the same stability and targeting properties of hormone-dependent cancers or of cancers of organs synthesizing steroidal hormones, as those of a formulation according to the present invention, as put forward in Example 3 below.

As the formulation according to the invention specifically targets hormone-dependent cancers, such as breast or prostate cancer, or cancers of organs synthesizing steroidal hormones, notably ovaries and adrenal glands, it may be used:

for treating them.
The therapeutic agent for treating hormone-dependent cancers or cancers of organs synthesizing steroidal hormones which it comprises may be specifically released at the hormone-dependent cancer or at the cancer of organs synthesizing steroidal hormones.

for diagnosing them.
The formulation according to the invention comprising a diagnostic agent may for example be used in per-operative imaging in order to assist the surgeon during resection of the tumor, since it gives the possibility of distinguishing the cancer areas, the possible metastases or sentinel nodes.

The formulation according to the invention may be used as such, or adapted to the targeted application, for example by dilution, for administration of therapeutic or diagnostic agent(s), in humans or in animals.

Because it may be exclusively prepared from constituents approved for humans, it is of particular interest for administration via a parenteral route. However, it is also possible to envision administration via other routes, notably orally, topically or via a vaginal route.

The described formulation thus allows access to a simple means for administering therapeutic agents required for treating hormone-dependant cancers or cancers of organs synthesizing steroidal hormones, via chemotherapy or phototherapy notably.

A therapeutic treatment method for hormone-dependent cancers or cancers of organs synthesizing steroidal hormones comprising the administration into a mammal, preferably a human, who is in need thereof, of a therapeutically effective amount of the formulation as defined above is also one of the objects of the present invention.

The invention will be described in more detail by means of the appended examples.

EXAMPLES

Example 1

Preparation of Formulations According to the Invention

The following preparation method was followed:
(i) Preparation of the Oily Phase:
Soy oil, Suppocire NC and lecithin were weighed and then mixed with dichloromethane before being heated to 60° C. in order to obtain a homogeneous viscous solution. Dichloromethane gives the possibility of promoting solubilization. The dichloromethane is then evaporated in vacuo. The compound(s) of formula (I) was (were) then added into the obtained oily phase.
(ii) Doping the Oily Phase:
A solution of the diagnostic agent (fluorophore) in ethanol was incorporated to the oily phase and the ethanol was then evaporated under a nitrogen flow for 5 mins. The mixture was maintained viscous via a water bath at 40° C./50° C.
(iii) Preparation of the Aqueous Phase:
During the phase for evaporating the ethanol, the aqueous phase was prepared. In a 5 ml Eppendorf, the co-surfactant, the glycerol and the aqueous PBS solution were mixed and then dissolved in a bath at 75° C.
(iv) Mixing Both Phases:
The oily phase was at about 40° C. (in viscous form) and the aqueous phase at about 70° C. (at the outlet of the bath). The aqueous phase was poured into the oily phase.
(v) Emulsification:
The flask containing both phases was attached in the sonication chamber. The base of the flask (about 1 cm) was positioned in a water bath at 15° C. The conical sonotrode is immersed in the flask, the latter being placed at half-height (over about 1 cm in the solution) for better homogeneity for making the emulsion. Sonication was then carried out with an AV505 Sonicator (Sonics, Newtown USA). The effective sonication duration was 10 mins.
(vi) Purification:
Purification was carried out by dialysis in a large volume of PBS 1× overnight. The glycerol is removed during this step. The purified nano-emulsion sample was taken and the volume was adjusted by adding sterile PBS 1× to the desired volume (13 ml). The whole of the sample was sterilized by filtration on a 0.22 µm filter.

Example 1.1.

A trebly Labelled Formulation Comprising Two Compounds of Formula (I) (Labelled Cholesteryl Oleate and Labelled Cholesteryl Hexadecyl Ether) and a Fluorophore as a Diagnostic Agent (DiD)

A formulation of the following composition was prepared:

TABLE 1

Composition of the formulation of Example 1.1.

| | | Raw material | Amount (2 ml batch) | % by mass of the total formulation | | % by mass of the dispersed phase (the co-surfactant belonging to the dispersed phase) |
|---|---|---|---|---|---|---|
| oily phase | amphiphilic lipid | Lipoid | 17 mg | 0.85 | i.e. 5.4% i.e. oily pre mix = 5.50% | 8.42% |
| | solubilizing lipid | Suppocire | 68 mg | 3.4 | | 33.66% |
| | oil | Soy oil | 23 mg | 1.15 | | 11.39% |
| | compound of formula (I) | [3H]CHE | 348 µCi | 0.045 | i.e. 0.10% | 0.45% |
| | compound of formula (I) | [14C]CO | 88 µCi | 0.015 | | 0.15% |
| | diagnostic agent | DiD | 400 µM | 0.04 | | 0.40% |
| aqueous phase | co-surfactant | PEG | 92 mg | 4.6 | — | 45.53% |
| | aqueous solution | PBS 1X | 1800 µL | 90 | — | — |
| | | Dispersed phase | 202.22 mg i.e. 100.11 mg/ml (rounded to 100 mg/ml) | 10.1 (rounded to 10) | — | 100% |

DiD is a fluorophore which may be detected by fluorescence.

The compounds [3H]CHE and [14C]CO are labelled cholesteryl hexadecylether and labelled cholesteryl oleate respectively and respectively have the following formulae:

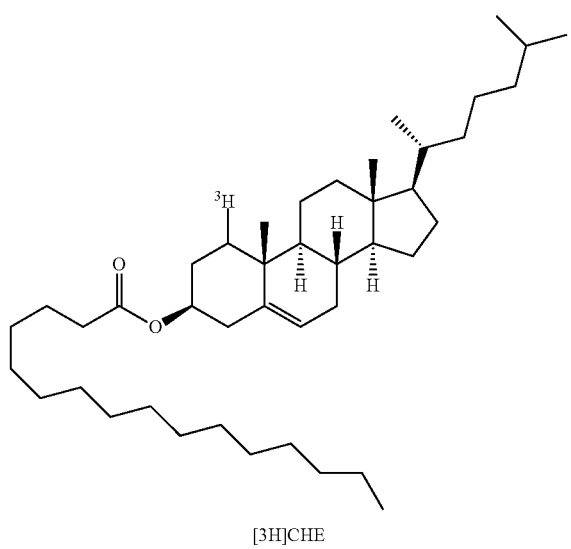

[3H]CHE

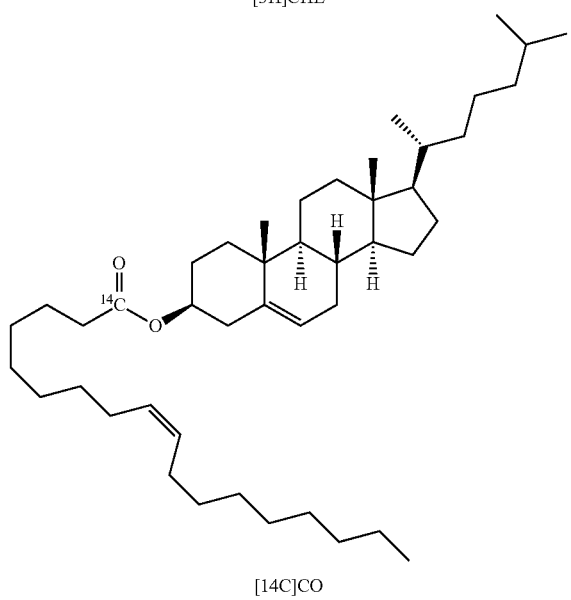

[14C]CO

As these compounds of formula (I) are labelled, they may be localized by measuring radioactivity.

The localization of the nano-emulsion of Example 1.1. may therefore be monitored by fluorescence or radioactivity.

Example 1.2.

A Formulation Comprising Cholesteryl Stearate as a Compound of Formula (I) and a Fluorophore as a Diagnostic Agent (DiD)

Formulations were prepared with the same compositions as those of Table 1, except that [3H]CHE and [14C]CO are replaced with:

0.6 wt % based on the total of the dispersed phase (considering that the co-surfactant belongs to the dispersed phase) of cholesteryl stearate (Example 1.2.1), or 2 wt % based on the total of the dispersed phase (considering that the co-surfactant belongs to the dispersed phase) of cholesteryl stearate (Example 1.2.2).

Cholesteryl stearate is designated by CHST hereafter.

In the following examples, the radioactivity was counted with the TRiCarb Counter (Ref: Packard, Liquid Scintillation Analyzers; Models 2200CA).

Fluobeam 700 (Fluoptics) is the apparatus with which the whole of the organs from the biodistribution were analyzed in fluorescence as well as the one with which the biodistribution kinetics of the nano-emulsions were established in vivo. This imaging system allows viewing of the fluorescence in spectral bands from 700 to 850 nm for a 650 nm excitation. The apparatus consists of an electric case containing the laser of class 3B, its power supply and an optical head containing the CCD camera.

In all the tables below, MEAN and STD respectively mean the average and the standard deviation of the measurements.

Example 2

In Vivo Result of the Biodistribution of the Formulations According to the Invention in FVB Female and Male Mice The nano-emulsions of Example 1 were injected into FVB female and male mice. As a comparison, a mixture of three tracers ([3H]CHE, [14C]CO and DiD) (not formulated as a nano-emulsion) was injected in order to observe the distribution of the tracers in the absence of droplets being used as a distribution carrier.

Example 2.1.

Biodistribution Result of the Formulation of Example 1.1.

Comparative Example: Non-Encapsulated Free Tracers

Tables 2 to 5 provide the results of the biodistribution of each tracer ([3H]CHE, [14C]CO and DiD) expressed as a percentage of the injected dose (for ([3H]CHE and [14C] CO) per gram of tissue or as fluorescence intensity (expressed as a number of photons per pixel and reduced to 100 ms of integration of the signal, and this in all the tables of the present application comprising fluorescence intensity values) (for DiD) depending on the organ of the mouse, 2 hours (Table 2), 6 hours (Table 3), 16 hours (Table 4) and 24 hours (Table 5) after injecting into an FVB female mouse a mixture of the three tracers ([3H]CHE, [14C]CO and DiD) non-formulated as a nano-emulsion (comparative data).

TABLE 2

|  | 2 h | | | | | |
|---|---|---|---|---|---|---|
|  | [3H]CHE | | [14C]CO | | DiD | |
|  | MEAN | STD | MEAN | STD | MEAN | STD |
| Liver | 1.76 | 0.80 | 4.79 | 1.51 | 2477.20 | 949.88 |
| Intestine | 0.03 | 0.04 | 0.76 | 0.28 | 451.58 | 98.27 |

TABLE 2-continued

| | 2 h | | | | | |
|---|---|---|---|---|---|---|
| | [3H]CHE | | [14C]CO | | DiD | |
| | MEAN | STD | MEAN | STD | MEAN | STD |
| Lung | 29.10 | 14.16 | 72.86 | 30.69 | 848.08 | 299.20 |
| Spleen | 1.55 | 0.40 | 3.65 | 0.61 | 1162.07 | 528.53 |
| Kidney | 0.09 | 0.05 | 0.89 | 0.41 | 862.35 | 55.97 |
| Fat | 0.02 | 0.02 | 0.69 | 0.49 | 280.30 | 82.36 |
| Ovary | 0.04 | 0.03 | 1.57 | 0.78 | 954.70 | 149.20 |
| Adrenal glands | 0.17 | 0.16 | 3.25 | 1.07 | 730.45 | 392.63 |
| Uterus | 0.02 | 0.01 | 0.49 | 0.05 | 694.28 | 549.88 |
| Brain | 0.00 | 0.00 | 0.23 | 0.08 | 439.56 | 61.39 |
| Heart | 0.08 | 0.08 | 0.59 | 0.09 | 487.37 | 101.42 |
| Muscle | 0.04 | 0.00 | 0.38 | 0.09 | 211.84 | 73.35 |
| Pancreas | 0.05 | 0.04 | 0.47 | 0.10 | 466.58 | 82.71 |
| Salivary gland | 0.01 | 0.02 | 0.74 | 0.38 | 399.58 | 178.76 |

TABLE 3

| | 6 h | | | | | |
|---|---|---|---|---|---|---|
| | [3H]CHE | | [14C]CO | | DiD | |
| | MEAN | STD | MEAN | STD | MEAN | STD |
| Liver | 3.23 | 1.88 | 5.53 | 3.71 | 2293.21 | 901.09 |
| Intestine | 0.15 | 0.11 | 1.21 | 0.37 | 363.09 | 127.53 |
| Lung | 83.99 | 53.84 | 142.66 | 81.34 | 433.52 | 111.50 |
| Spleen | 3.35 | 1.64 | 3.53 | 2.11 | 3224.12 | 645.77 |
| Kidney | 0.41 | 0.17 | 1.36 | 0.49 | 573.78 | 97.58 |
| Fat | 0.05 | 0.10 | 1.05 | 0.37 | 234.61 | 88.10 |
| Ovary | 0.07 | 0.08 | 2.12 | 0.20 | 250.27 | 338.83 |
| Adrenal glands | 0.36 | 0.23 | 3.56 | 0.36 | 208.14 | 196.51 |
| Uterus | 0.04 | 0.01 | 0.46 | 0.09 | 506.03 | 78.54 |
| Brain | 0.02 | 0.02 | 0.26 | 0.04 | 116.17 | 78.03 |
| Heart | 0.30 | 0.18 | 1.21 | 0.59 | 346.63 | 60.44 |
| Muscle | 0.03 | 0.03 | 0.53 | 0.16 | 108.34 | 29.11 |
| Pancreas | 0.09 | 0.04 | 0.76 | 0.13 | 191.73 | 50.40 |
| Salivary gland | 0.09 | 0.01 | 1.15 | 0.14 | 232.98 | 151.37 |

TABLE 4

| | 16 h | | | | | |
|---|---|---|---|---|---|---|
| | [3H]CHE | | [14C]CO | | DiD | |
| | MEAN | STD | MEAN | STD | MEAN | STD |
| Liver | 6.95 | 0.79 | 11.86 | 2.81 | 2954.59 | 420.30 |
| Intestine | 0.13 | 0.05 | 1.09 | 0.33 | 505.69 | 190.99 |
| Lung | 124.35 | 61.28 | 261.87 | 130.59 | 370.94 | 27.96 |
| Spleen | 4.17 | 0.17 | 5.32 | 1.21 | 3403.29 | 953.61 |
| Kidney | 0.53 | 0.06 | 1.82 | 0.26 | 382.29 | 194.01 |
| Fat | 0.02 | 0.02 | 1.39 | 0.38 | 295.69 | 118.05 |
| Ovary | 0.19 | 0.16 | 1.64 | 0.39 | 729.53 | 604.29 |
| Adrenal gland | 0.47 | 0.22 | 4.24 | 1.01 | 1683.36 | 399.48 |
| Uterus | 0.03 | 0.02 | 1.00 | 0.27 | 665.40 | 284.46 |
| Brain | 0.02 | 0.02 | 0.30 | 0.07 | −24.23 | 53.01 |
| Heart | 0.35 | 0.17 | 1.87 | 0.13 | 186.72 | 102.04 |
| Muscle | 0.05 | 0.01 | 0.43 | 0.15 | 93.88 | 56.25 |
| Pancreas | 0.04 | 0.04 | 1.00 | 0.07 | 101.87 | 104.38 |
| Salivary gland | 0.05 | 0.05 | 1.29 | 0.22 | 271.01 | 172.82 |

TABLE 5

| | 24 h | | | | | |
|---|---|---|---|---|---|---|
| | [3H]CHE | | [14C]CO | | DiD | |
| | MEAN | STD | MEAN | STD | MEAN | STD |
| Liver | 1.12 | 0.93 | 3.29 | 3.51 | 2663.45 | 439.54 |
| Intestine | 0.07 | 0.04 | 0.81 | 0.28 | 354.94 | 252.57 |
| Lung | 6.37 | 6.75 | 29.91 | 34.49 | 300.36 | 72.13 |
| Spleen | 10.63 | 15.66 | 2.27 | 1.90 | 3880.70 | 147.54 |
| Kidney | 1.12 | 1.69 | 1.02 | 0.43 | 397.90 | 234.64 |
| Fat | 1.42 | 2.36 | 1.64 | 0.39 | 344.99 | 37.37 |
| Ovary | 0.08 | 0.07 | 1.40 | 0.51 | 989.32 | 137.18 |
| Adrenal gland | 0.31 | 0.25 | 2.60 | 0.77 | 653.68 | 140.78 |
| Uterus | 0.34 | 0.53 | 0.62 | 0.12 | 636.69 | 101.11 |
| Brain | 0.03 | 0.05 | 0.22 | 0.03 | 57.68 | 51.05 |
| Heart | 0.12 | 0.05 | 0.82 | 0.37 | 285.67 | 92.94 |
| Muscle | 0.11 | 0.01 | 0.79 | 0.27 | 289.03 | 383.41 |
| Pancreas | 0.03 | 0.02 | 0.95 | 0.63 | 158.45 | 65.37 |
| Salivary gland | 0.14 | 0.13 | 0.86 | 0.50 | 187.28 | 176.21 |

Tables 2 to 5 show a strong accumulation of the free radioactive tracers ([3H]CHE and [14C]CO) in the lungs. Strong accumulation in the liver and the spleen is observed for the tracer DiD alone.

Nano-emulsion According to Example 1.1. Injected into an FVB Female Mouse

Tables 6 to 14 provide the biodistribution results of each tracer ([3H]CHE, [14C]CO and DiD) expressed as a percentage of the dose injected per gram of tissue (or [3H]CHE and [14C]CO) or as fluorescence intensity (for DiD) depending on the organ of the mouse, 15 minutes (Table 6), 2 hours (Table 7), 4 hours (Table 8), 6 hours (Table 9), 16 hours (Table 10), 24 hours (Table 11), 72 hours (Table 12), 120 hours (Table 13) and 168 hours (Table 14), after injection into an FVB female mouse of the nano-emulsion of Example 1.1. (nano-emulsion according to the invention comprising the three tracers ([3H]CHE, [14C]CO and DiD).

TABLE 6

| | 15 min | | | | | |
|---|---|---|---|---|---|---|
| | [3H]CHE | | [14C]CO | | DiD | |
| Organs | MEAN | STD | MEAN | STD | MEAN | STD |
| Liver | 8.26 | 1.27 | 8.86 | 1.85 | 979 | 174 |
| Intestine | 1.71 | 0.87 | 1.75 | 0.81 | 300 | 262 |
| Lung | 3.91 | 1.65 | 3.92 | 1.81 | 618 | 391 |
| Spleen | 3.63 | 0.88 | 3.58 | 0.82 | 727 | 182 |
| Kidney | 4.09 | 2.70 | 4.20 | 2.76 | 228 | 125 |
| Fat | 1.10 | 0.54 | 1.15 | 0.51 | 147 | 130 |
| Ovary | 5.38 | 3.33 | 4.59 | 2.62 | 484 | 616 |
| Adrenal glands | 10.60 | 3.57 | 10.18 | 2.89 | 457 | 366 |
| Uterus | 0.90 | 0.29 | 0.93 | 0.29 | 178 | 142 |
| Brain | 0.476 | 0.047 | 0.499 | 0.052 | 145 | 55 |
| Heart | 8.303 | 6.540 | 8.676 | 6.814 | 451 | 136 |
| Muscle | 0.675 | 0.677 | 0.744 | 0.824 | 1 | 11 |
| Pancreas | 1.233 | 0.298 | 1.262 | 0.244 | 216 | 145 |
| Salivary glands | 1.157 | 0.562 | 1.057 | 0.312 | 59 | 190 |

TABLE 7

| | 2 h | | | | | |
|---|---|---|---|---|---|---|
| | [3H]CHE | | [14C]CO | | DiD | |
| Organs | MEAN | STD | MEAN | STD | MEAN | STD |
| Liver | 31.09 | 4.34 | 19.41 | 3.24 | 1421 | 142 |
| Intestine | 2.44 | 0.13 | 2.33 | 0.19 | 637 | 377 |
| Lung | 4.44 | 1.49 | 4.42 | 1.25 | 727 | 406 |
| Spleen | 5.10 | 1.10 | 2.87 | 0.42 | 805 | 304 |
| Kidneys | 3.83 | 0.29 | 3.91 | 0.23 | 473 | 70 |
| Fat | 0.76 | 0.17 | 3.85 | 1.04 | 247 | 102 |
| Ovary | 29.28 | 14.72 | 22.72 | 12.69 | 1807 | 661 |
| Adrenal glands | 21.12 | 4.59 | 18.50 | 3.42 | 1050 | 340 |
| Uterus | 2.23 | 0.11 | 2.21 | 0.20 | 814 | 50 |
| Brain | 0.26 | 0.09 | 0.29 | 0.08 | 250 | 120 |
| Heart | 4.64 | 1.18 | 4.41 | 1.17 | 389 | 157 |
| Muscle | 0.45 | 0.12 | 0.48 | 0.09 | 213 | 28 |
| Pancreas | 1.43 | 0.10 | 1.68 | 0.15 | 399 | 59 |
| Salivary glands | 1.42 | 0.70 | 1.74 | 0.56 | 288 | 221 |

TABLE 8

| | 4 h | | | | | |
|---|---|---|---|---|---|---|
| | [3H]CHE | | [14C]CO | | DiD | |
| Organs | MEAN | STD | MEAN | STD | MEAN | STD |
| Liver | 37.43 | 5.51 | 13.69 | 1.62 | 1845 | 245 |
| Intestine | 2.46 | 0.56 | 1.80 | 0.39 | 974 | 152 |
| Lungs | 4.02 | 0.34 | 3.09 | 0.19 | 925 | 81 |
| Spleen | 5.00 | 0.93 | 1.97 | 0.22 | 955 | 19 |
| Kidney | 2.51 | 0.32 | 2.27 | 0.34 | 614 | 108 |
| Fat | 1.40 | 1.17 | 1.46 | 0.44 | 522 | 311 |
| Ovary | 39.41 | 11.65 | 25.14 | 6.94 | 2781 | 181 |
| Adrenal glands | 28.13 | 3.23 | 21.37 | 3.98 | 1754 | 385 |
| Uterus | 1.69 | 1.42 | 1.39 | 1.11 | 712 | 538 |
| Brain | 0.19 | 0.02 | 0.23 | 0.04 | 279 | 74 |
| Heart | 4.94 | 1.05 | 3.75 | 0.49 | 550 | 87 |
| Muscle | 0.41 | 0.11 | 0.38 | 0.09 | 236 | 64 |
| Pancreas | 1.01 | 0.26 | 1.17 | 0.18 | 527 | 138 |
| Salivary glands | 1.09 | 0.19 | 1.47 | 0.13 | 516 | 114 |

TABLE 9

| | 16 h | | | | | |
|---|---|---|---|---|---|---|
| | [3H]CHE | | [14C]CO | | DiD | |
| Organs | MEAN | STD | MEAN | STD | MEAN | STD |
| Liver | 47.67 | 7.58 | 8.68 | 3.35 | 1661 | 342 |
| Intestine | 4.87 | 0.93 | 2.53 | 0.37 | 1139 | 290 |
| Lungs | 4.63 | 1.97 | 2.80 | 0.94 | 592 | 169 |
| Spleen | 7.48 | 0.51 | 1.89 | 0.19 | 978 | 434 |
| Kidney | 2.06 | 0.15 | 1.75 | 0.08 | 627 | 79 |
| Fat | 1.36 | 0.86 | 8.06 | 1.53 | 532 | 248 |
| Ovary | 52.26 | 2.35 | 21.45 | 2.85 | 2915 | 184 |
| Adrenal glands | 43.16 | 14.73 | 30.64 | 9.04 | 2355 | 328 |
| Uterus | 3.91 | 1.01 | 2.76 | 0.98 | 1759 | 1216 |
| Brain | 0.13 | 0.01 | 0.13 | 0.01 | 259 | 42 |
| Heart | 3.49 | 0.66 | 2.00 | 0.41 | 444 | 123 |
| Muscle | 0.76 | 0.26 | 1.59 | 0.48 | 289 | 43 |
| Pancreas | 1.17 | 0.44 | 1.19 | 0.35 | 564 | 233 |
| Salivary glands | 1.27 | 0.79 | 2.02 | 1.05 | 641 | 238 |

TABLE 10

| | 24 h | | | | | |
|---|---|---|---|---|---|---|
| | [3H]CHE | | [14C]CO | | DiD | |
| Organs | MEAN | STD | MEAN | STD | MEAN | STD |
| Liver | 48.76 | 7.87 | 5.39 | 1.95 | 1675 | 299 |
| Intestine | 2.78 | 1.00 | 1.22 | 0.20 | 777 | 215 |
| Lung | 3.21 | 0.55 | 1.30 | 0.29 | 667 | 124 |
| Spleen | 7.50 | 2.34 | 1.10 | 0.11 | 774 | 85 |
| Kidney | 1.50 | 0.40 | 1.03 | 0.22 | 599 | 47 |
| Fat | 0.88 | 0.43 | 2.28 | 1.08 | 553 | 472 |
| Ovary | 38.06 | 14.16 | 9.58 | 2.88 | 3173 | 370 |
| Adrenal glands | 39.68 | 14.88 | 13.05 | 4.09 | 2624 | 460 |
| Uterus | 1.82 | 0.87 | 0.96 | 0.48 | 971 | 474 |
| Brain | 0.09 | 0.01 | 0.11 | 0.01 | 239 | 40 |
| Heart | 3.53 | 0.62 | 1.31 | 0.25 | 288 | 54 |
| Muscle | 0.46 | 0.17 | 1.01 | 0.53 | 161 | 52 |
| Pancreas | 0.64 | 0.13 | 0.67 | 0.04 | 446 | 113 |
| Salivary glands | 1.40 | 0.61 | 1.76 | 0.07 | 411 | 186 |

TABLE 11

| | 48 h | | | | | |
|---|---|---|---|---|---|---|
| | [3H]CHE | | [14C]CO | | DiD | |
| Organs | MEAN | STD | MEAN | STD | MEAN | STD |
| Liver | 58.43 | 2.25 | 1.53 | 0.37 | 1868 | 258 |
| Intestine | 4.43 | 0.38 | 1.01 | 0.04 | 481 | 77 |
| Lungs | 3.91 | 0.21 | 1.28 | 0.10 | 212 | 39 |
| Spleen | 12.32 | 2.48 | 1.03 | 0.05 | 342 | 71 |
| Kidney | 1.63 | 0.19 | 0.77 | 0.08 | 555 | 305 |
| Fat | 1.05 | 0.26 | 3.46 | 2.81 | 208 | 31 |
| Ovary | 36.42 | 8.45 | 6.46 | 1.12 | 4018 | 668 |
| Adrenal glands | 42.26 | 1.49 | 10.83 | 0.49 | 1484 | 607 |
| Uterus | 3.75 | 2.06 | 1.24 | 0.51 | 951 | 697 |
| Brain | 0.08 | 0.01 | 0.11 | 0.00 | 51 | 47 |
| Heart | 3.52 | 0.23 | 0.87 | 0.04 | 122 | 72 |
| Muscle | 0.36 | 0.05 | 0.34 | 0.18 | 32 | 39 |
| Pancreas | 1.00 | 0.29 | 0.70 | 0.21 | 202 | 102 |
| Salivary glands | 1.09 | 0.16 | 1.20 | 0.61 | 268 | 103 |

TABLE 12

| | 72 h | | | | | |
|---|---|---|---|---|---|---|
| | [3H]CHE | | [14C]CO | | DiD | |
| Organs | MEAN | STD | MEAN | STD | MEAN | STD |
| Liver | 39.73 | 8.94 | 0.75 | 0.11 | 1136 | 392 |
| Intestine | 3.58 | 1.96 | 0.62 | 0.23 | 297 | 115 |
| Lungs | 2.95 | 0.54 | 0.88 | 0.18 | 120 | 169 |
| Spleen | 7.65 | 3.13 | 0.75 | 0.21 | 330 | 172 |
| Kidney | 1.27 | 0.30 | 0.66 | 0.09 | 365 | 129 |
| Fat | 0.85 | 0.14 | 5.01 | 3.51 | 159 | 51 |
| Ovary | 25.11 | 6.58 | 3.04 | 0.81 | 2397 | 325 |
| Adrenal glands | 36.92 | 14.04 | 9.36 | 5.06 | 1135 | 586 |
| Uterus | 5.63 | 5.79 | 1.00 | 0.66 | 514 | 552 |
| Brain | 0.08 | 0.02 | 0.10 | 0.02 | 43 | 35 |
| Heart | 2.98 | 0.88 | 0.64 | 0.19 | 113 | 26 |
| Muscle | 0.22 | 0.04 | 0.28 | 0.05 | 3 | 47 |
| Pancreas | 0.74 | 0.20 | 0.50 | 0.12 | 102 | 38 |
| Salivary glands | 1.10 | 0.27 | 1.16 | 0.43 | 237 | 114 |

TABLE 13

| | 120 h | | | | | |
|---|---|---|---|---|---|---|
| | [3H]CHE | | [14C]CO | | DiD | |
| Organs | MEAN | STD | MEAN | STD | MEAN | STD |
| Liver | 39.13 | 3.21 | 0.42 | 0.03 | 996 | 280 |
| Intestine | 3.60 | 0.24 | 0.28 | 0.03 | 279 | 24 |
| Lungs | 3.30 | 0.75 | 0.57 | 0.05 | 53 | 55 |
| Spleen | 9.69 | 1.34 | 0.45 | 0.04 | 229 | 98 |
| Kidney | 1.29 | 0.12 | 0.40 | 0.05 | 383 | 59 |
| Fat | 0.68 | 0.10 | 2.42 | 1.32 | 176 | 65 |
| Ovary | 16.92 | 11.11 | 1.24 | 0.50 | 2319 | 815 |
| Adrenal gland | 41.92 | 8.51 | 6.43 | 0.63 | 1688 | 136 |
| Uterus | 4.99 | 3.67 | 0.62 | 0.41 | 563 | 507 |
| Brain | 0.08 | 0.00 | 0.08 | 0.00 | 90 | 36 |
| Heart | 2.59 | 0.54 | 0.37 | 0.03 | 80 | 32 |
| Muscle | 0.27 | 0.02 | 0.30 | 0.05 | 254 | 348 |
| Pancreas | 1.00 | 0.34 | 0.40 | 0.16 | 297 | 49 |
| Salivary glands | 2.14 | 0.84 | 1.78 | 1.01 | 120 | 339 |

TABLE 14

| | 168 h | | | | | |
|---|---|---|---|---|---|---|
| | [3H]CHE | | [14C]CO | | DiD | |
| Organs | MEAN | STD | MEAN | STD | MEAN | STD |
| Liver | 32.70 | 6.86 | 0.28 | 0.01 | 676.60 | 14.849 |
| Intestine | 2.80 | 0.80 | 0.18 | 0.02 | 214.02 | 23.794 |
| Lungs | 1.70 | 0.14 | 0.25 | 0.06 | 1.35 | 0.120 |
| Spleen | 10.71 | 0.49 | 0.28 | 0.00 | 171.93 | 88.862 |
| Kidneys | 1.44 | 0.19 | 0.28 | 0.03 | 391.45 | 128.679 |
| Fat | 0.99 | 0.14 | 5.02 | 2.61 | 164.55 | 115.690 |
| Ovary | 20.61 | 4.67 | 0.74 | 0.08 | 1614.45 | 387.463 |
| Adrenal glands | 29.30 | 3.35 | 2.73 | 0.04 | 660.62 | 704.034 |
| Uterus | 4.86 | 0.63 | 0.37 | 0.03 | 697.92 | 378.217 |
| Brain | 0.07 | 0.02 | 0.07 | 0.00 | 40.28 | 1.563 |
| Heart | 2.19 | 0.44 | 0.22 | 0.03 | 117.29 | 17.600 |
| Muscle | 0.37 | 0.19 | 0.32 | 0.08 | 16.21 | 54.384 |
| Pancreas | 0.79 | 0.12 | 0.23 | 0.00 | 125.11 | 68.066 |
| Salivary glands | 2.01 | 0.93 | 1.14 | 0.19 | 216.84 | 196.130 |

A comparison of the values of Tables 2 to 5 and of Tables 6 to 14 shows that the biodistribution is different when free tracers are injected or when the nano-emulsion according to Example 1.1 is injected. In the case of the use of a nano-emulsion according to the invention, the three tracers go to the same location at the same moment after an elapsed period of about 12h post-injection, which demonstrates the carrier effect (targeting) of the droplets of the nano-emulsion according to the invention.

An accumulation of droplets of the nano-emulsion according to the invention is observed in the liver (metabolization area of lipid nano-droplets) as well as in steroidal organs (ovaries and adrenal glands), which are organs synthesizing steroidal hormones. These same areas are again found in cancer tissues of hormone-dependent cancers, such as for example certain breast or prostate cancers.

A slight fluorescence signal is observed in the uterus. It was observed, after dissection and histology, that following the period of the cycle of the mouse, the morphology of the uterus changes as well as its self-fluorescence which becomes higher. Thus, these results would stem from self-fluorescence of the uterus.

As a preferential accumulation in the ovaries and adrenal glands was observed, fluorescence images were produced in cryohistology. The fluorescence images at 680 nm confirmed the accumulation of the droplets of the nano-emulsion in these organs. The histological images of the ovaries show accumulation in the corpus luteum, which has the function of secreting progesterone. The histological images of the adrenal glands show accumulation in the cortical area which ensures secretion of the steroids.

Nano-emulsion According to Example 1.1. Injected into an FVB Male Mouse

Tables 15 to 21 provide the results of the biodistribution of each tracer ([3H]CHE, [14C]CO and DiD) expressed as a percentage of the dose injected per gram of tissue (for [3H]CHE and [14C]CO) or as fluorescence intensity (for DiD) depending on the organ of the mouse, 15 minutes (Table 6), 2 hours (Table 7), 4 hours (Table 8), 6 hours (Table 9), 16 hours (Table 10), 24 hours (Table 11), 72 hours (Table 12), 120 hours (Table 13) and 168 hours (Table 14), after injection into an FVB male mouse of the nano-emulsion of Example 1.1. comprising the three tracers ([3H]CHE, [14C]CO and DiD).

TABLE 15

| | 2 h | | | | | |
|---|---|---|---|---|---|---|
| | [3H]CHE | | [14C]CO | | DiD | |
| | Mean | STD | Mean | STD | Mean | STD |
| Liver | 22.67 | 1.50 | 11.13 | 1.40 | 831.9 | 234.8 |
| Intestine | 2.44 | 0.17 | 2.05 | 0.25 | 392.1 | 78.3 |
| Lung | 5.08 | 0.80 | 4.45 | 0.90 | 559.9 | 124.5 |
| Spleen | 7.15 | 0.49 | 2.97 | 0.36 | 455.7 | 216.8 |
| Kidney | 5.29 | 0.90 | 6.10 | 1.35 | 601.1 | 79.7 |
| Fat | 1.14 | 0.19 | 1.62 | 0.44 | 184.0 | 31.0 |
| Testicle | 1.36 | 0.12 | 1.34 | 0.12 | 639.9 | 141.0 |
| Adrenal gland | 10.16 | 2.47 | 8.63 | 3.25 | 779.1 | 21.6 |
| Seminal glands | 0.79 | 0.28 | 0.80 | 0.28 | 175.3 | 64.6 |
| Brain | 0.35 | 0.03 | 0.40 | 0.05 | 186.5 | 47.7 |
| Heart | 9.84 | 1.09 | 9.28 | 1.36 | 427.6 | 55.3 |
| Muscle | 0.99 | 0.24 | 0.94 | 0.27 | 176.7 | 54.4 |
| Pancreas | 1.64 | 0.15 | 1.72 | 0.09 | 255.1 | 99.4 |
| Salivary gland | 1.53 | 0.25 | 1.99 | 0.37 | 310.0 | 97.2 |

TABLE 16

| | 4 h | | | | | |
|---|---|---|---|---|---|---|
| | [3H]CHE | | [14C]CO | | DiD | |
| | Mean | STD | Mean | STD | Mean | STD |
| Liver | 17.25 | 5.85 | 5.76 | 1.18 | 813.0 | 71.6 |
| Intestine | 1.98 | 0.68 | 1.49 | 0.50 | 336.2 | 108.5 |
| Lung | 2.98 | 1.44 | 2.30 | 1.04 | 446.4 | 105.1 |
| Spleen | 5.31 | 1.82 | 2.08 | 0.41 | 407.4 | 151.7 |
| Kidney | 3.14 | 0.96 | 3.36 | 1.13 | 505.0 | 127.1 |
| Fat | 0.74 | 0.20 | 0.71 | 0.15 | 128.3 | 55.5 |
| Testicle | 1.35 | 0.33 | 1.26 | 0.29 | 470.9 | 283.7 |
| Adrenal gland | 16.96 | 7.65 | 15.01 | 5.05 | 536.1 | 177.9 |
| Seminal gland | 0.50 | 0.17 | 0.52 | 0.16 | 179.5 | 39.8 |
| Brain | 0.23 | 0.07 | 0.24 | 0.06 | 150.6 | 28.3 |
| Heart | 7.57 | 2.16 | 6.07 | 1.93 | 306.9 | 52.4 |
| Muscle | 0.56 | 0.06 | 0.51 | 0.02 | 152.3 | 56.0 |
| Pancreas | 1.50 | 0.40 | 1.54 | 0.43 | 295.0 | 58.7 |
| Salivary gland | 1.26 | 0.20 | 1.70 | 0.18 | 297.8 | 130.0 |

TABLE 17

| | 6 h | | | | | |
|---|---|---|---|---|---|---|
| | [3H]CHE | | [14C]CO | | DiD | |
| | Mean | STD | Mean | STD | Mean | STD |
| Liver | 22.609 | 3.289 | 5.926 | 0.706 | 847.4 | 301.5 |
| Intestine | 2.549 | 0.564 | 1.778 | 0.434 | 378.0 | 54.4 |
| Lung | 3.771 | 0.541 | 2.790 | 0.325 | 426.0 | 181.2 |
| Spleen | 6.453 | 1.102 | 2.025 | 0.135 | 488.6 | 129.1 |
| Kidney | 3.336 | 0.460 | 3.841 | 0.775 | 427.7 | 68.0 |
| Fat | 1.234 | 0.574 | 1.217 | 0.633 | 221.1 | 69.1 |
| Testicle | 2.000 | 0.632 | 1.839 | 0.642 | 723.1 | 112.0 |
| Adrenal gland | 13.399 | 2.214 | 10.940 | 1.302 | 721.9 | 38.7 |
| Seminal gland | 0.54 | 0.16 | 0.59 | 0.19 | 261.0 | 32.1 |
| Brain | 0.24 | 0.04 | 0.28 | 0.04 | 235.9 | 42.1 |
| Heart | 8.52 | 0.69 | 6.10 | 0.23 | 253.8 | 75.3 |
| Muscle | 0.77 | 0.10 | 0.58 | 0.04 | 169.3 | 40.2 |
| Pancreas | 1.67 | 0.32 | 1.55 | 0.38 | 347.0 | 90.3 |
| Salivary gland | 2.10 | 1.24 | 1.95 | 0.52 | 488.5 | 50.8 |

TABLE 18

| | 16 h | | | | | |
|---|---|---|---|---|---|---|
| | [3H]CHE | | [14C]CO | | DiD | |
| | Mean | STD | Mean | STD | MEAN | STD |
| Liver | 40.91 | 1.28 | 3.55 | 0.34 | 1157.2 | 433.7 |
| Intestine | 5.19 | 0.59 | 2.13 | 0.21 | 640.4 | 298.4 |
| Lung | 5.31 | 0.91 | 2.14 | 0.42 | 423.5 | 94.4 |
| Spleen | 9.19 | 1.06 | 1.25 | 0.14 | 373.3 | 96.6 |
| Kidney | 2.40 | 0.31 | 2.01 | 0.26 | 343.0 | 61.3 |
| Fat | 1.70 | 1.13 | 2.24 | 0.88 | 117.0 | 6.5 |
| Testicle | 2.95 | 0.50 | 2.14 | 0.41 | 525.4 | 119.1 |
| Adrenal gland | 32.89 | 1.11 | 17.48 | 5.45 | 1086.2 | 242.6 |
| Seminal gland | 0.64 | 0.21 | 0.77 | 0.33 | 163.0 | 128.4 |
| Brain | 0.18 | 0.01 | 0.17 | 0.01 | 134.7 | 73.7 |
| Heart | 8.50 | 0.94 | 3.22 | 0.21 | 281.5 | 85.1 |
| Muscle | 0.97 | 0.25 | 0.72 | 0.20 | 281.9 | 83.9 |
| Pancreas | 1.92 | 0.60 | 1.35 | 0.37 | 332.6 | 131.2 |
| Salivary gland | 2.68 | 0.17 | 2.11 | 0.35 | 838.8 | 227.5 |

TABLE 19

| | 24 h | | | | | |
|---|---|---|---|---|---|---|
| | [3H]CHE | | [14C]CO | | DiD | |
| | Mean | STD | Mean | STD | MEAN | STD |
| Liver | 30.93 | 7.18 | 2.05 | 0.42 | 1152.7 | 120.1 |
| Intestine | 3.41 | 0.80 | 1.18 | 0.22 | 621.0 | 64.0 |
| Lung | 2.88 | 0.80 | 1.08 | 0.03 | 406.0 | 28.6 |
| Spleen | 6.65 | 1.60 | 0.80 | 0.12 | 638.0 | 197.6 |
| Kidney | 1.80 | 0.26 | 1.11 | 0.11 | 323.1 | 10.6 |
| Fat | 0.83 | 0.50 | 0.60 | 0.33 | 142.1 | 54.5 |
| Ovary | 1.71 | 1.29 | 1.08 | 0.66 | 575.9 | 104.8 |
| Adrenal gland | 17.41 | 5.59 | 7.78 | 3.66 | 1105.9 | 126.9 |
| Seminal gland | 0.35 | 0.28 | 0.30 | 0.24 | 170.6 | 43.2 |
| Brain | 0.11 | 0.03 | 0.12 | 0.03 | 109.3 | 16.6 |
| Heart | 5.76 | 2.10 | 1.72 | 0.71 | 239.7 | 17.6 |
| Muscle | 0.38 | 0.31 | 0.38 | 0.08 | 144.9 | 28.5 |
| Pancreas | 1.31 | 0.12 | 1.14 | 0.57 | 268.9 | 38.7 |
| Salivary gland | 1.57 | 0.78 | 1.69 | 1.21 | 501.1 | 155.2 |

TABLE 20

| | 48 h | | | | | |
|---|---|---|---|---|---|---|
| | [3H]CHE | | [14C]CO | | DiD | |
| | Mean | STD | Mean | STD | MEAN | STD |
| Liver | 24.53 | 0.76 | 0.70 | 0.13 | 988.2 | 149.5 |
| Intestine | 3.50 | 0.61 | 0.55 | 0.03 | 381.6 | 116.6 |
| Lung | 3.02 | 0.02 | 0.67 | 0.10 | 346.5 | 115.9 |
| Spleen | 11.18 | 3.50 | 0.76 | 0.01 | 656.7 | 132.2 |
| Kidney | 1.77 | 0.44 | 0.82 | 0.34 | 168.3 | 34.4 |
| Fat | 0.94 | 0.18 | 0.85 | 0.34 | 185.1 | 62.2 |
| Testicle | 2.97 | 0.40 | 0.97 | 0.14 | 648.6 | 246.3 |
| Adrenal gland | 25.12 | 2.72 | 8.12 | 2.67 | 783.7 | 240.6 |
| Seminal gland | 0.35 | 0.28 | 0.30 | 0.24 | 166.7 | 47.5 |
| Brain | 0.10 | 0.00 | 0.10 | 0.01 | 160.4 | 25.8 |
| Heart | 6.05 | 0.99 | 0.97 | 0.07 | 178.1 | 102.8 |
| Muscle | 0.63 | 0.08 | 0.27 | 0.04 | 131.7 | 28.7 |
| Pancreas | 0.99 | 0.18 | 0.49 | 0.11 | 266.2 | 82.1 |
| Salivary gland | 2.07 | 0.21 | 1.54 | 0.20 | 489.7 | 53.1 |

TABLE 21

| | 72 h | | | | | |
|---|---|---|---|---|---|---|
| | [3H]CHE | | [14C]CO | | DiD | |
| | Mean | STD | Mean | STD | MEAN | STD |
| Liver | 24.97 | 2.51 | 0.61 | 0.08 | 648.0 | 103.1 |
| Intestine | 3.47 | 0.62 | 0.49 | 0.12 | 267.8 | 33.8 |
| Lung | 3.04 | 0.41 | 0.67 | 0.06 | 286.6 | 104.7 |
| Spleen | 6.40 | 2.62 | 0.48 | 0.15 | 278.0 | 68.4 |
| Kidney | 1.82 | 0.39 | 0.78 | 0.07 | 160.3 | 23.1 |
| Fat | 0.70 | 0.12 | 1.87 | 0.55 | 78.0 | 11.3 |
| Testicle | 4.34 | 1.62 | 1.43 | 0.47 | 481.2 | 105.0 |
| Adrenal gland | 46.41 | 8.98 | 14.65 | 0.95 | 717.3 | 268.8 |
| Seminal gland | 0.58 | 0.03 | 0.47 | 0.03 | 74.4 | 1.3 |
| Brain | 0.11 | 0.02 | 0.10 | 0.01 | 14.8 | 8.6 |
| Heart | 7.83 | 3.47 | 0.88 | 0.35 | 142.3 | 43.0 |
| Muscle | 0.49 | 0.20 | 0.35 | 0.21 | 109.2 | 23.0 |
| Pancreas | 1.12 | 0.36 | 0.63 | 0.19 | 160.6 | 22.1 |
| Salivary gland | 2.36 | 0.42 | 1.38 | 0.66 | 430.2 | 8.2 |

A comparison of the values of Tables 6 to 14 and of Tables 15 to 21 shows that the biodistribution in vivo between females and males is identical as regards the accumulation in the liver and in the adrenal glands.

Example 2.2.

Biodistribution Result of the Formulation of Example 1.2.

Table 22 provides the biodistribution results of DiD expressed as fluorescence intensity depending on the organ of the mouse 4 hours after injection into a FVB female mouse of the nano-emulsion of Example 1.2.1. or 1.2.2. comprising the tracer DiD and cholesteryl stearate (CHST) as a compound of formula (I).

TABLE 22

| % of cholesteryl stearate in the dispersed phase | 0% (compound without the compound of formula (I)) (comparative example) | | 0.6% CHST (Example 1.2.1.) | | 2% CHST (Example 1.2.2.) | |
|---|---|---|---|---|---|---|
| | MEAN | STD | MEAN | STD | MEAN | STD |
| Brain | 249.8 | 62.0 | 303 | 86 | 280 | 79 |
| Heart | 619.6 | 69.1 | 549 | 134 | 624 | 38 |
| Liver | 1585.5 | 270.9 | 1598 | 294 | 1992 | 305 |
| Fat | 299.4 | 52.9 | 426 | 166 | 342 | 70 |
| Intestine | 532.4 | 68.1 | 627 | 249 | 548 | 92 |
| Muscle | 198.9 | 22.7 | 235 | 87 | 136 | 43 |
| Ovary | 1286.6 | 47.2 | 2440 | 491 | 2671 | 659 |
| Pancreas | 353.8 | 89.9 | 472 | 120 | 284 | 7 |
| Lung | 602.8 | 115.5 | 960 | 213 | 878 | 123 |
| Spleen | 730.2 | 142.5 | 737 | 99 | 669 | 48 |
| Kidney | 796.8 | 106.8 | 886 | 185 | 747 | 8 |
| Salivary gland | 707.7 | 258.7 | 404 | 181 | 320 | 63 |
| Adrenal gland | 1780.2 | 560.2 | 1498 | 527 | 1476 | 899 |
| Uterus | 1379.6 | 680.5 | 1177 | 45 | 1165 | 534 |

Like in Example 2.2., accumulation is observed in the liver (metabolization area of lipid nano-droplets) as well as in the steroidal organs (ovaries and adrenal glands), organs synthesizing steroidal hormones. These same areas synthesizing steroidal hormones are again found in cancer tissues of hormone-dependent cancers, such as for example certain breast or prostate cancers.

Example 3

Comparison of the Formulations According to the Invention and of Formulations Comprising Cholesterol Instead of the Compound of Formula (I)

Stability Tests

Stability tests at 4° C. were conducted for formulations either comprising or not a diagnostic agent (DiD) and either comprising cholesteryl stearate (compound of formula (I)) (0.6%, 2% and 3% by weight based on the weight of the dispersed phase), or cholesterol (0.6% 2%, 5% or 10% by weight based on the weight of the dispersed phase) instead of the compound of formula (I).

In the absence of a diagnostic agent, beyond 90 days, increases in the size of the dispersed phase droplets and in the polydispersity index (DPI) were observed for formulations comprising 2%, 5% and 10% of cholesterol based on the weight of the dispersed phase, which indicates a lack of stability of these formulations. On the other hand, the size of the dispersed phase droplets and the polydispersity index of the formulations according to the invention remain constant beyond 150 days, which indicates that these formulations are stable.

In the presence of the diagnostic agent, for the formulation comprising cholesterol, it was observed that the more the cholesterol level increases, the more the encapsulation level of the diagnostic agent decreases. There again, destabilization of these formulations beyond 90 days at 4° C. was observed. On the other hand, no encapsulation difference of DiD and no stability problem were observed for formulations comprising cholesteryl stearate (formulations according to the invention).

Thus, a formulation comprising more than 0.6% by weight of cholesterol based on the weight of the dispersed phase is not stable beyond 90 days at 4° C., while formulations according to the invention comprising a compound of formula (I) are stable beyond 150 days for all the tested concentrations and allow better encapsulation of the diagnostic agent and formulations comprising cholesterol.

Without intending to be bound to a particular theory, it seems that the cholesterol is located at the interface of the lipid phase droplets and destabilizes them, while the compounds of formula (I), which are more liphophilic than the cholesterol by the group R, are located in the core of the droplets and do not affect the stability of the nano-emulsion. In Vivo Biodistribution Test, 4 Hours after Injection into an FVB Female Mouse.

Tables 23 to 28 provide the biodistribution results (fluorescence intensity depending on the organ of the mouse) 4 hours after injection into an FVB female mouse of nano-emulsions comprising DiD (fluorescent tracer) and:
  without any cholesterol or one of its derivatives (control nano-emulsion),
  comprising cholesterol (comparative nano-emulsions), or
  comprising a compound of formula (I) (nano-emulsions according to the invention, according to Examples 1.1., 1.2.1. or 1.2.2.).

TABLE 23 fluorescence intensity according to the organ of the mouse 4 hours after injection into an FVB female mouse of a nano-emulsion comprising DiD (tracer) and 0 (control), 0.6%, 2%, 5% or 10% of cholesterol based on the weight of the dispersed phase and (comparative nano-emulsions).

| % of cholesterol in the dispersed phase | Cholesterol-fluorescence intensity-4 h post injection into an FVB female mouse | | | | | | | | | |
|---|---|---|---|---|---|---|---|---|---|---|
| | 0 (control) | | 0.6 (comparative) | | 2 (comparative) | | 5 (comparative) | | 10 (comparative) | |
| | MEAN | STD | MEAN | STD | MEAN | STD | MEAN | STD | MEAN | STD |
| Brain | 249.8 | 62.0 | 116.6 | 44.7 | 288.9 | 12.5 | 308.0 | 132.5 | 149.3 | 79.4 |
| Heart | 619.6 | 69.1 | 419.3 | 73.7 | 493.2 | 63.4 | 273.9 | 31.9 | 291.2 | 137.2 |
| Liver | 1585.5 | 270.9 | 1146.5 | 129.9 | 1392.6 | 262.6 | 1487.4 | 17.0 | 1459.8 | 670.9 |
| Fat | 299.4 | 52.9 | 355.5 | 98.5 | 257.6 | 31.7 | 237.1 | 60.1 | 261.3 | 79.3 |
| Intestine | 532.4 | 68.1 | 651.3 | 98.8 | 612.7 | 72.1 | 559.3 | 114.2 | 467.6 | 219.1 |
| Muscle | 198.9 | 22.7 | 140.3 | 43.0 | 207.9 | 45.0 | 301.0 | 263.2 | 120.7 | 71.2 |
| Ovary | 1286.6 | 47.2 | 718.4 | 230.7 | 1427.5 | 472.0 | 1540.8 | 247.9 | 1659.4 | 702.6 |

TABLE 23-continued fluorescence intensity according to the organ of the mouse 4 hours after injection
into an FVB female mouse of a nano-emulsion comprising DiD (tracer) and 0 (control), 0.6%,
2%, 5% or 10% of cholesterol based on the weight of the dispersed phase and (comparative
nano-emulsions).

| % of cholesterol in the dispersed phase | Cholesterol-fluorescence intensity-4 h post injection into an FVB female mouse | | | | | | | | |
|---|---|---|---|---|---|---|---|---|---|
| | 0 (control) | | 0.6 (comparative) | | 2 (comparative) | | 5 (comparative) | | 10 (comparative) | |
| | MEAN | STD | MEAN | STD | MEAN | STD | MEAN | STD | MEAN | STD |
| Pancreas | 353.8 | 89.9 | 260.0 | 35.2 | 332.7 | 12.1 | 270.5 | 88.9 | 202.3 | 147.8 |
| Lung | 602.8 | 115.5 | 561.9 | 56.5 | 483.9 | 76.7 | 385.9 | 134.5 | 660.1 | 236.5 |
| Spleen | 730.2 | 142.5 | 632.0 | 57.6 | 700.6 | 117.2 | 747.4 | 185.9 | 467.6 | 185.0 |
| Kidney | 796.8 | 106.8 | 647.7 | 129.9 | 657.9 | 77.8 | 546.1 | 48.9 | 402.9 | 257.9 |
| Salivary gland | 707.7 | 258.7 | 209.6 | 170.6 | 368.9 | 54.6 | 240.9 | 144.0 | 111.6 | 204.8 |
| Adrenal gland | 1780.2 | 560.2 | 1316.0 | 213.9 | 941.0 | 126.1 | 1039.5 | 558.4 | 1445.5 | 627.3 |
| Uterus | 1379.6 | 680.5 | 842.4 | 173.6 | 1016.1 | 303.0 | 1122.6 | 603.6 | 497.2 | 463.1 |

TABLE 24 the ratio of fluorescence intensity in an organ of the mouse over the fluorescence
intensity in the muscles 4 hours after injection into an FVB female mouse of a nano-emulsion
comprising DiD (tracer) and 0 (control), 0.6%, 2%, 5% or 10% of cholesterol based on the
weight of the dispersed phase and (comparative nano-emulsions).

| % of cholesterol in the dispersed phase | Cholesterol-organ/muscle ratio-4 h post-injection into an FVB female mouse | | | | | | | | |
|---|---|---|---|---|---|---|---|---|---|
| | 0 (control) | | 0.6 (comparative) | | 2 (comparative) | | 5 (comparative) | | 10 (comparative) | |
| | MEAN | STD | MEAN | STD | MEAN | STD | MEAN | STD | MEAN | STD |
| Brain | 1.2 | 0.3 | 0.8 | 0.1 | 1.4 | 0.3 | 2.0 | 0.8 | 1.3 | 0.1 |
| Heart | 3.1 | 0.3 | 3.3 | 1.7 | 2.5 | 0.8 | 1.8 | 0.1 | 2.6 | 0.6 |
| Liver | 8.3 | 1.2 | 8.9 | 3.8 | 7.0 | 2.4 | 10.1 | 1.5 | 12.8 | 1.8 |
| Fat | 1.5 | 0.2 | 2.8 | 1.3 | 1.3 | 0.2 | 1.6 | 0.2 | 2.8 | 2.0 |
| Intestine | 2.8 | 0.3 | 4.9 | 1.4 | 3.1 | 0.8 | 3.9 | 1.3 | 4.1 | 0.6 |
| Muscle | 1.0 | 0.0 | 1.0 | 0.0 | 1.0 | 0.0 | 1.0 | 0.0 | 1.0 | 0.0 |
| Ovary | 6.7 | 0.7 | 4.4 | 1.8 | 6.8 | 1.4 | 10.6 | 3.0 | 14.8 | 2.7 |
| Pancreas | 1.8 | 0.4 | 2.0 | 0.9 | 1.7 | 0.5 | 1.8 | 0.6 | 1.7 | 0.5 |
| Lung | 3.2 | 0.6 | 4.2 | 1.0 | 2.5 | 1.0 | 2.5 | 0.5 | 6.1 | 1.6 |
| Spleen | 3.8 | 0.6 | 4.8 | 1.3 | 3.5 | 0.7 | 5.0 | 1.0 | 4.2 | 0.9 |
| Kidney | 4.1 | 0.4 | 5.2 | 3.0 | 3.2 | 0.6 | 3.7 | 0.3 | 3.3 | 0.2 |
| Salivary gland | 3.8 | 1.4 | 1.3 | 1.0 | 1.8 | 0.3 | 1.6 | 1.0 | 0.5 | 1.1 |
| Adrenal gland | 10.1 | 4.4 | 12.4 | 6.8 | 4.6 | 0.4 | 6.7 | 2.6 | 12.8 | 2.2 |
| Uterus | 7.7 | 3.7 | 6.3 | 1.5 | 4.8 | 0.7 | 7.2 | 2.8 | 3.3 | 2.3 |

TABLE 25 fluorescence intensity depending on the organ of the mouse 4 hours after injection
into an FVB female mouse of the nano-emulsion comprising DiD (tracer) and 0 (control),
0.6%, 2%, 5% or 10% of cholesterol based on the weight of the dispersed phase and
(comparative nano-emulsions).

| % of CH or of CHST In dispersed phase | Cholesterol (CH) or cholesteryl stearate (CHST)-fluorescence intensity-4 h post-injection into an FVB female mouse | | | | | | | | |
|---|---|---|---|---|---|---|---|---|---|
| | 0% CH (control) | | 0.6% (comparative) | | 2% CH (comparative) | | 0.6% CHST (Example 1.2.1.) | | 2% CHST (Example 1.2.2.) | |
| | MEAN | STD | MEAN | STD | MEAN | STD | MEAN | STD | MEAN | STD |
| Brain | 249.8 | 62.0 | 116.6 | 44.7 | 288.9 | 12.5 | 303 | 86 | 280 | 79 |
| Heart | 619.6 | 69.1 | 419.3 | 73.7 | 493.2 | 63.4 | 549 | 134 | 624 | 38 |
| Liver | 1585.5 | 270.9 | 1146.5 | 129.9 | 1392.6 | 262.6 | 1598 | 294 | 1992 | 305 |
| Fat | 299.4 | 52.9 | 355.5 | 98.5 | 257.6 | 31.7 | 426 | 166 | 342 | 70 |
| Intestine | 532.4 | 68.1 | 651.3 | 98.8 | 612.7 | 72.1 | 627 | 249 | 548 | 92 |
| Muscle | 198.9 | 22.7 | 140.3 | 43.0 | 207.9 | 45.0 | 235 | 87 | 136 | 43 |
| Ovary | 1286.6 | 47.2 | 718.4 | 230.7 | 1427.5 | 472.0 | 2440 | 491 | 2671 | 659 |
| Pancreas | 353.8 | 89.9 | 260.0 | 35.2 | 332.7 | 12.1 | 472 | 120 | 284 | 7 |
| Lung | 602.8 | 115.5 | 561.9 | 56.5 | 483.9 | 76.7 | 960 | 213 | 878 | 123 |

TABLE 25-continued fluorescence intensity depending on the organ of the mouse 4 hours after injection
into an FVB female mouse of the nano-emulsion comprising DiD (tracer) and 0 (control),
0.6%, 2%, 5% or 10% of cholesterol based on the weight of the dispersed phase and
(comparative nano-emulsions).

Cholesterol (CH) or cholesteryl stearate (CHST)-fluorescence intensity-
4 h post-injection into an FVB female mouse

| % of CH or of CHST In dispersed phase | 0% CH (control) | | 0.6% (comparative) | | 2% CH (comparative) | | 0.6% CHST (Example 1.2.1.) | | 2% CHST (Example 1.2.2.) | |
|---|---|---|---|---|---|---|---|---|---|---|
| | MEAN | STD | MEAN | STD | MEAN | STD | MEAN | STD | MEAN | STD |
| Spleen | 730.2 | 142.5 | 632.0 | 57.6 | 700.6 | 117.2 | 737 | 99 | 669 | 48 |
| Kidney | 796.8 | 106.8 | 647.7 | 129.9 | 657.9 | 77.8 | 886 | 185 | 747 | 8 |
| Salivary gland | 707.7 | 258.7 | 209.6 | 170.6 | 368.9 | 54.6 | 404 | 181 | 320 | 63 |
| Adrenal gland | 1780.2 | 560.2 | 1316.0 | 213.9 | 941.0 | 126.1 | 1498 | 527 | 1476 | 899 |
| Uterus | 1379.6 | 680.5 | 842.4 | 173.6 | 1016.1 | 303.0 | 1177 | 45 | 1165 | 534 |

TABLE 26 ratio of the fluorescence intensity in an organ of the mouse over the fluorescence
intensity in the muscles 4 hours after injection into an FVB female mouse of a nano-emulsion
comprising DiD (tracer) and 0 (control), 0.6% or 2% of cholesterol based on the weight of the
dispersed phase (comparative nano-emulsions) or 0.6% or 2% of cholesteryl stearate based
on the weight of the dispersed phase (nano-emulsions according to the invention).

Cholesterol (CH) or cholesteryl stearate (CHST)-organ/muscle ratio-
4 h post -injection into FVB female mouse

| % of CH or of CHST In dispersed phase | 0 % (control) | | 0.6% CH (comparative) | | 2% CH (comparative) | | 0.6% CHST (Example 1.2.1.) | | 2% CHST (Example 1.2.2.) | |
|---|---|---|---|---|---|---|---|---|---|---|
| | MEAN | STD | MEAN | STD | MEAN | STD | MEAN | STD | MEAN | STD |
| Brain | 1.2 | 0.3 | 0.8 | 0.1 | 1.4 | 0.3 | 1.3 | 0.2 | 2.1 | 0.1 |
| Heart | 3.1 | 0.3 | 3.3 | 1.7 | 2.5 | 0.8 | 2.4 | 0.4 | 4.8 | 1.2 |
| Liver | 8.3 | 1.2 | 8.9 | 3.8 | 7.0 | 2.4 | 7.3 | 2.6 | 15.1 | 2.6 |
| Fat | 1.5 | 0.2 | 2.8 | 1.3 | 1.3 | 0.2 | 1.8 | 0.3 | 2.7 | 1.4 |
| Intestine | 2.8 | 0.3 | 4.9 | 1.4 | 3.1 | 0.8 | 2.7 | 0.1 | 4.4 | 2.1 |
| Muscle | 1.0 | 0.0 | 1.0 | 0.0 | 1.0 | 0.0 | 1.0 | 0.0 | 1.0 | 0.0 |
| Ovary | 6.7 | 0.7 | 4.4 | 1.8 | 6.8 | 1.4 | 10.9 | 3.0 | 19.9 | 1.5 |
| Pancreas | 1.8 | 0.4 | 2.0 | 0.9 | 1.7 | 0.5 | 2.3 | 1.2 | 2.2 | 0.6 |
| Lung | 3.2 | 0.6 | 4.2 | 1.0 | 2.5 | 1.0 | 4.4 | 1.9 | 7.0 | 3.1 |
| Spleen | 3.8 | 0.6 | 4.8 | 1.3 | 3.5 | 0.7 | 3.4 | 1.2 | 5.1 | 1.3 |
| Kidney | 4.1 | 0.4 | 5.2 | 3.0 | 3.2 | 0.6 | 4.1 | 1.4 | 5.8 | 1.9 |
| Salivary gland | 3.8 | 1.4 | 1.3 | 1.0 | 1.8 | 0.3 | 1.7 | 0.1 | 2.6 | 1.3 |
| Adrenal gland | 10.1 | 4.4 | 12.4 | 6.8 | 4.6 | 0.4 | 6.5 | 1.6 | 10.3 | 3.3 |
| Uterus | 7.7 | 3.7 | 6.3 | 1.5 | 4.8 | 0.7 | 7.6 | 2.2 | 7.6 | 2.2 |

TABLE 27 fluorescence intensity according to the organ of the mouse 4 hours after injection
into an FVB female mouse of the nano-emulsion comprising DiD (tracer) and 0 (control),
0.6% or 2% of cholesteryl stearate based on the weight of the dispersed phase (nano-
emulsion according to the invention) or 0.6% of the set ([3H]CHE/[14C]CO) based on the
weight of the dispersed phase (nano-emulsions according to the invention).

[3H]CHE and [14C]CO or cholesteryl stearate-fluorescence intensity-
4 h post-injection into an FVB female mouse

| % of cholesteryl derivative in the dispersed phase | 0.45% of [3H]CHE and 0.15% of [14C]CO (Example 1.1.) | | 0 (control) | | 0.6% CHST (Example 1.2.1.) | | 2% CHST (Example 1.2.2.) | |
|---|---|---|---|---|---|---|---|---|
| | MEAN | STD | MEAN | STD | MEAN | STD | MEAN | STD |
| Brain | 279 | 74 | 249.8 | 62.0 | 303 | 86 | 280 | 79 |
| Heart | 550 | 87 | 619.6 | 69.1 | 549 | 134 | 624 | 38 |
| Liver | 1845 | 245 | 1585.5 | 270.9 | 1598 | 294 | 1992 | 305 |
| Fat | 522 | 311 | 299.4 | 52.9 | 426 | 166 | 342 | 70 |

TABLE 27-continued fluorescence intensity according to the organ of the mouse 4 hours after injection into an FVB female mouse of the nano-emulsion comprising DiD (tracer) and 0 (control), 0.6% or 2% of cholesteryl stearate based on the weight of the dispersed phase (nano-emulsion according to the invention) or 0.6% of the set ([3H]CHE/[14C]CO) based on the weight of the dispersed phase (nano-emulsions according to the invention).

| % of cholesteryl derivative in the dispersed phase | 0.45% of [3H]CHE and 0.15% of [14C]CO (Example 1.1.) | | 0 (control) | | 0.6% CHST (Example 1.2.1.) | | 2% CHST (Example 1.2.2.) | |
|---|---|---|---|---|---|---|---|---|
| | MEAN | STD | MEAN | STD | MEAN | STD | MEAN | STD |
| Intestine | 974 | 152 | 532.4 | 68.1 | 627 | 249 | 548 | 92 |
| Muscle | 236 | 64 | 198.9 | 22.7 | 235 | 87 | 136 | 43 |
| Ovary | 2781 | 181 | 1286.6 | 47.2 | 2440 | 491 | 2671 | 659 |
| Pancreas | 527 | 138 | 353.8 | 89.9 | 472 | 120 | 284 | 7 |
| Lung | 955 | 19 | 602.8 | 115.5 | 960 | 213 | 878 | 123 |
| Spleen | 614 | 108 | 730.2 | 142.5 | 737 | 99 | 669 | 48 |
| Kidney | 925 | 81 | 796.8 | 106.8 | 886 | 185 | 747 | 8 |
| Salivary gland | 516 | 114 | 707.7 | 258.7 | 404 | 181 | 320 | 63 |
| Adrenal gland | 1754 | 385 | 1780.2 | 560.2 | 1498 | 527 | 1476 | 899 |
| Uterus | 712 | 538 | 1379.6 | 680.5 | 1177 | 45 | 1165 | 534 |

TABLE 28 ratio of the fluorescence intensity in an organ of the mouse over the fluorescence intensity in the muscles 4 hours after injection into an FVB female mouse of a nano-emulsion comprising DiD (tracer) and 0 (control), 0.6% or 2% of cholesteryl stearate based on the weight of the dispersed phase (nano-emulsions according to the invention) or 0.6% of the set ([3H]CHE/[14C]CO) based on the weight of the dispersed phase (nano-emulsion according to the invention).

| % of cholesterol In the Dispersed phase | 0,45% of [3H]CHE And 0.15% of [14C]CO (Example 1.1.) | | 0 (control) | | 0,6% CHST (Example 1.2.1.) | | 2% CHST (Example 1.2.2.) | |
|---|---|---|---|---|---|---|---|---|
| | MEAN | STD | MEAN | STD | MEAN | STD | MEAN | STD |
| Brain | 1.2 | 0.1 | 1.2 | 0.3 | 1.3 | 0.2 | 2.1 | 0.1 |
| Heart | 2.4 | 0.6 | 3.1 | 0.3 | 2.4 | 0.4 | 4.8 | 1.2 |
| Liver | 8.1 | 1.4 | 8.3 | 1.2 | 7.3 | 2.6 | 15.1 | 2.6 |
| Fat | 2.1 | 0.8 | 1.5 | 0.2 | 1.8 | 0.3 | 2.7 | 1.4 |
| Intestine | 4.5 | 1.8 | 2.8 | 0.3 | 2.7 | 0.1 | 4.4 | 2.1 |
| Muscle | 1.0 | 0.0 | 1.0 | 0.0 | 1.0 | 0.0 | 1.0 | 0.0 |
| Ovary | 12.3 | 2.8 | 6.7 | 0.7 | 10.9 | 3.0 | 19.9 | 1.5 |
| Pancreas | 2.3 | 0.4 | 1.8 | 0.4 | 2.3 | 1.2 | 2.2 | 0.6 |
| Lung | 4.3 | 1.3 | 3.2 | 0.6 | 4.4 | 1.9 | 7.0 | 3.1 |
| Spleen | 2.7 | 0.3 | 3.8 | 0.6 | 3.4 | 1.2 | 5.1 | 1.3 |
| Kidney | 4.1 | 0.9 | 4.1 | 0.4 | 4.1 | 1.4 | 5.8 | 1.9 |
| Salivary gland | 2.2 | 0.4 | 3.8 | 1.4 | 1.7 | 0.1 | 2.6 | 1.3 |
| Adrenal gland | 8.0 | 3.8 | 10.1 | 4.4 | 6.5 | 1.6 | 10.3 | 3.3 |
| Uterus | 3.6 | 3.7 | 7.7 | 3.7 | 7.6 | 2.2 | 7.6 | 2.2 |

* = trebly labelled

An increase in the intensity of the signal in the ovaries is observed at cholesterol encapsulation levels of more than 5% based on the weight of the dispersed phase. It is therefore necessary to use at least 5% by weight of cholesterol based on the weight of the dispersed phase in order to observe a more specific targeting towards the steroidal organs than towards the other organs. It should be noted that at low cholesterol levels, the signal is even less than that of the formulation without any cholesterol (0%).

Now, as shown above in stability tests, a formulation of at least 5% of cholesterol based on the weight of the dispersed phase (required proportion for beginning to observe specific targeting of hormone-dependent cancers) is not stable. Now, stability is an essential condition for industrial application.

By comparison, the in vivo biodistribution tests at 4 h post-injection of formulations comprising 0.6% and 2% by weight of cholesteryl stearate based on the weight of the dispersed phase and of DiD in healthy FVB mice (formulation according to the invention) shown in Example 2 above show that these formulations specifically target ovaries, even with a low cholesteryl stearate level (0.6% by weight based on the weight of the dispersed phase).

The comparison of the biodistribution results show that the same targeting intensity is obtained in the ovaries for concentrations of 5% by weight of cholesterol based on the weight of the dispersed phase and 0.6% by weight of cholesteryl stearate based on the weight of the dispersed phase, and that the signal with 2% by weight of cholesteryl stearate based on the weight of the dispersed phase is greater than that of the formulation comprising 10% by weight of cholesterol based on the weight of the dispersed phase. For a same concentration of diagnostic agents, at least five times more, generally eight times more cholesterol than of a compound of formula (I) are required for obtaining the same intensity for targeting steroidal organs.

The formulation according to the invention comprising a compound of formula (I) therefore allows much more specific targeting of steroidal organs than a formulation comprising cholesterol.

Example 4

Comparison of the Specificity of the Targeting between a Hormone-Dependent Cancer (Breast Cancer) and a Non-Hormone-Dependent Cancer (Brain Cancer—Glioma Model)

Two types of cancer models were studied: the glioma model (brain cancer) and the PyMT model (breast cancer). The kinetics of the accumulation of droplets of the nano-emulsion according to Example 1.1. in the tumor of an FVB female mouse were evaluated.

In the FVB-implanted PyMT (breast cancer) model, fast accumulation of the signal was observed in the tumoral area. As soon as 5h post-injection, a tumor/muscle ratio of 3.5 is observed. The fluorescence intensity maximum is observed at 21 h post-injection with a tumor/muscle signal ratio of 9. After 21h, the signal begins to decrease.

On the other hand, the accumulation in the tumoral areas is much slower in the model of the glioma. The maximum fluorescence intensity is observed 48h post-injection versus 21h post-injection for the PyMT FVB model.

These results show that the nano-emulsion preferentially targets hormone-dependent cancers relatively to non-hormone-dependent cancers.

Example 5

Influence of the Weight Proportion of the Compound of Formula (I) Based on the Weight of Dispersed Phase on the Possibility of Formulating the Nano-Emulsion An attempt was made for preparing nano-emulsions with mass proportions of cholesteryl stearate based on the total weight of the dispersed phase, greater than those of the nano-emulsions according to Examples 1.2.1.and 1.2.2. described above (comprising 0.6% and 2% of cholesteryl stearate respectively based on the total weight of the dispersed phase), i.e. with 3%, 6%, 16% and 33% of cholesteryl stearate based on the total weight of the dispersed phase.

TABLE 29 composition of formulations and possibility of formulating the nano-emulsion according to the mass proportion of cholesteryl stearate based on the total weight of the dispersed phase.

| | | Raw material | Ex 1.2.1. | Ex 1.2.2. | Ex 5.1. | Ex 5.2. | Ex 5.3. | Ex 5.4. |
|---|---|---|---|---|---|---|---|---|
| Oily phase | Amphiphilic lipid | Lipoid | | | | 17 mg | | |
| | Solubilizing lipid | Suppocire | | | | 68 mg | | |
| | oil | Soy oil | | | | 23 mg | | |
| | Compound of formula (I) | CHST | 1.2 mg | 4 mg | 6 mg | 12 mg | 40 mg | 100 mg |
| | Mass % age of the compound of formula (I) in the dispersed phase (considering that the co-surfactant belongs to the dispersed phase) | | 0.60% | 1.96% | 2.91% | 5.66% | 16.67% | 33.33% |
| Aqueous phase | co-surfactant | PEG | | | | 92 mg | | |
| | aqueous solution | PBS 1X | | | | 1800 μL | | |
| | Possibility of formulating the nano-emulsion | | yes | yes | yes | no | no | no |

As illustrated in Table 29, it was not possible to formulate nano-emulsions for cholesteryl stearate proportions greater than 3% based on the total weight of the dispersed phase.

The invention claimed is:

1. A formulation of a therapeutic or diagnostic agent in the form of a nano-emulsion, comprising a continuous aqueous phase and at least one dispersed oily phase, wherein:

the oily phase comprises:
at least one amphiphilic lipid,
at least one solubilizing lipid,
at least one compound of the following formula (I):

(R-L)$_n$-A  (I), wherein :
n represents an integer from 1 to 5
L represents a simple bond or a divalent group selected from —O—, —COO—, —OOC—, —CO—NR'—, —NR'—CO—, —S—, —NR'—CO—NR'—, —O—CO—O—,
wherein R' and R" represent independently H or a linear or branched alkyl with 1 to 20 carbon atoms and
R represents a linear or branched alkyl comprising at least 11 carbon atoms or a linear or branched alkenyl comprising at least 11 carbon atoms, and
A represents a steriodic or sterolic group, and
the aqueous phase includes at least one co-surfactant comprising at least one chain consisting of alkylene oxide units;

the proportion of the compound of formula (I) being from 0.05% to 3% by weight based on the weight of the dispersed oily phase, the weight of the dispersed oily phase including the weight of the co-surfactant.

2. The formulation of a therapeutic or diagnostic agent according to claim 1, wherein the oily phase comprises at least one therapeutic agent for treating hormone-dependent cancers or cancers of organs synthesizing steroidal hormones, or one diagnostic agent.

3. The formulation of a therapeutic or diagnostic agent according to claim 1, wherein the group A is a group having one of the following formulae:

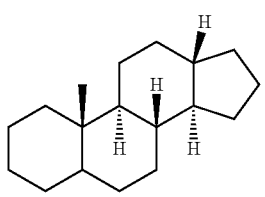

(IIa)

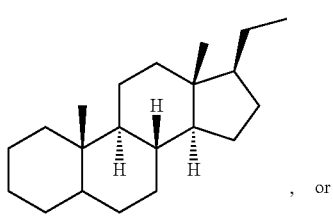

(IIb), or

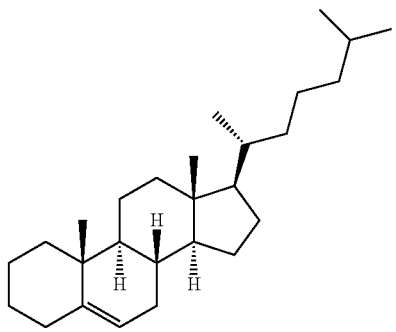

(IIc)

wherein one or several of the carbon atoms are substituted with an -L-R group as defined in claim 1.

4. The formulation of a therapeutic or diagnostic agent according to claim 1, wherein L represents —O— or —COO—.

5. The formulation of a therapeutic or diagnostic agent according to claim 1, wherein the amphiphilic lipid is a phospholipid.

6. The formulation of a therapeutic or diagnostic agent according to claim 1, wherein the solubilizing lipid comprises at least one glyceride of fatty acids.

7. The formulation of a therapeutic or diagnostic agent according to claim 6, wherein the solubilizing lipid comprises a mixture of saturated fatty acid glycerides including:
at least 10% by weight of C12 fatty acids,
at least 5% by weight of C14 fatty acids,
at least 5% by weight of C16 fatty acids, and
at least 5% by weight of C18 fatty acids.

8. The formulation of a therapeutic or diagnostic agent according to claim 1, wherein the oily phase further includes at least one oil.

9. The formulation of a therapeutic or diagnostic agent according to claim 1, wherein the co-surfactant includes at least one chain consisting of ethylene oxide or ethylene oxide and propylene oxide units.

10. The formulation of a therapeutic agent according to claim 1, comprising a therapeutic agent for treating hormone-dependent cancers or cancers of organs synthesizing steroidal hormones selected from the group consisting of:
agonists of gonadotropin releasing hormone,
antagonists of aromatase,
anti-estrogens, and
anti-androgens.

11. The formulation of a diagnostic agent according to claim 1, wherein the diagnostic agent is selected from the group consisting of a liphophilic fluorophore, fatty acid analogs, phospholipids functionalized with a fluorescent group, amphiphilic derivatives of dialkylcarbocyanines, fluorescent probes derived from sphingolipids, steroids or lipopolysaccharides, amphiphilic derivatives of cyanines, rhodamines, fluoresceins or cumarins, and diphenylhexatriene and its derivatives.

12. A method for preparing a formulation of a therapeutic or diagnostic agent in the form of a nano-emulsion according to claim 1, comprising at least one continuous aqueous phase and at least one dispersed oily phase, comprising:
(i) preparing the oily phase comprising at least one solubilizing lipid, at least one amphiphilic lipid, optionally at least one therapeutic or diagnostic agent and at least one compound of formula (I);

(ii) preparing an aqueous phase comprising a polyalkoxylated co-surfactant;
(iii) dispersing the oily phase in the aqueous phase under the action of sufficient shearing for forming a nano-emulsion; and
(iv) recovering the thereby formed nano-emulsion.

13. A therapeutic treatment method for hormone-dependent cancers, or cancers of organs synthesizing steroidal hormones comprising administering to a mammal in need thereof a therapeutically effective amount of the formulation of a therapeutic agent according to claim 1.

14. A method for diagnosing hormone-dependent cancers or cancers of organs synthesizing steroidal hormones comprising administering to a subject a formulation of a diagnostic agent according to claim 1.

15. The formulation of a therapeutic agent according to claim 10, comprising a therapeutic agent for treating hormone-dependent cancers or cancers of organs synthesizing steroidal hormones selected from the group consisting of estrogen, progestins, Formestane, Exemestane, Aminoglutethimide, Anastrozole, Fadrozole, Letrozole, Megestrol acetate, Medroxyprogesterone acetate, Mifepristone, Tamoxifene, Fulvestrant, abiraterone acetate and cyproterone acetate.

16. The formulation of a diagnostic agent according to claim 11, wherein the diagnostic agent is indocyanine green or 1,1'-dioctadecyl-3,3,3',3'-tetramethylindodicarbocyanine perchlorate.

17. The therapeutic treatment method according to claim 13, wherein the method is used to treat breast cancer, prostate cancer, cancer of the ovaries, or cancer of the adrenal glands.

18. The method for diagnosing according to claim 14, wherein the method is used to diagnose breast cancer, prostate cancer, cancer of the ovaries, or cancer of the adrenal glands.

* * * * *